(12) United States Patent
Eugene et al.

(10) Patent No.: US 11,285,032 B2
(45) Date of Patent: Mar. 29, 2022

(54) GRIP ENHANCEMENT AND PROTECTION FOR THE FEET

(71) Applicant: Gryppers, Inc., Raleigh, NC (US)

(72) Inventors: Jamelle Brian Eugene, Raleigh, NC (US); Precious Wilson, Durham, NC (US)

(73) Assignee: GRYPPERS, INC., Raleigh, NC (US)

( * ) Notice: Subject to any disclaimer, the term of this patent is extended or adjusted under 35 U.S.C. 154(b) by 127 days.

(21) Appl. No.: 16/697,469

(22) Filed: Nov. 27, 2019

(65) Prior Publication Data

US 2020/0100927 A1  Apr. 2, 2020

Related U.S. Application Data

(63) Continuation-in-part of application No. 15/927,231, filed on Mar. 21, 2018, now abandoned.

(60) Provisional application No. 62/475,115, filed on Mar. 22, 2017.

(51) Int. Cl.
*A61F 5/01* (2006.01)
*A41B 11/00* (2006.01)

(52) U.S. Cl.
CPC ............ *A61F 5/019* (2013.01); *A41B 11/003* (2013.01); *A41B 11/008* (2013.01); *A61F 5/0111* (2013.01); *A41B 2400/32* (2013.01); *A41B 2500/10* (2013.01); *A41B 2500/20* (2013.01); *A41B 2500/50* (2013.01)

(58) Field of Classification Search
CPC ..... A61F 5/019; A41B 11/003; A41B 11/004; A43B 7/1475; A43B 7/223; A43B 7/26
See application file for complete search history.

(56) References Cited

U.S. PATENT DOCUMENTS

| | | | | |
|---|---|---|---|---|
| 1,665,030 A | * | 4/1928 | Hartwig | A61F 5/019 602/30 |
| 2,596,038 A | * | 5/1952 | Mayer | A61F 5/019 602/30 |
| 3,049,120 A | * | 8/1962 | Marcus | A61F 5/019 602/30 |
| 4,632,103 A | * | 12/1986 | Fabricant | A61F 5/019 602/30 |
| 4,644,940 A | * | 2/1987 | Nakamura | A61F 5/019 128/882 |
| 4,856,505 A | * | 8/1989 | Shaffer | A61F 13/068 602/30 |
| 5,092,347 A | * | 3/1992 | Shaffer | A61F 13/064 128/892 |
| 5,282,782 A | * | 2/1994 | Kasahara | A61F 5/019 602/30 |
| 5,437,616 A | * | 8/1995 | Kasahara | A61F 5/019 128/894 |

(Continued)

*Primary Examiner* — Richale L Quinn
(74) *Attorney, Agent, or Firm* — Neo IP

(57) ABSTRACT

This document presents a footwear article that covers the foot and ankle of the wearer. The footwear object protects the wearer's feet and ankle while improving blood circulation, and supporting the toes, arches, and ankles of the wearer. The footwear object is manufactured of layered fabrics that are knitted and/or woven from both man-made and natural fibers. The footwear object has portions providing compression, padding, and grip to provide support and prevent injury to the wearer's feet and ankles.

20 Claims, 22 Drawing Sheets

(56) References Cited

U.S. PATENT DOCUMENTS

| | | | | |
|---|---|---|---|---|
| 5,617,585 | A * | 4/1997 | Fons | A41B 11/007 2/239 |
| 5,708,985 | A * | 1/1998 | Ogden | D04B 1/04 2/239 |
| 5,772,621 | A * | 6/1998 | Unruh | A61F 5/019 602/30 |
| 5,928,173 | A | 7/1999 | Unruh | |
| 6,016,575 | A * | 1/2000 | Prychak | A41B 11/004 2/239 |
| 6,093,163 | A * | 7/2000 | Chong | A61F 5/019 602/30 |
| 6,446,267 | B1 * | 9/2002 | Shah | A41B 11/005 2/239 |
| 6,499,320 | B1 * | 12/2002 | Bernhardt | A41B 11/00 66/178 R |
| 6,606,750 | B2 * | 8/2003 | Solwey | A41B 11/00 2/239 |
| 6,908,445 | B2 * | 6/2005 | Watts | A61F 5/0111 602/23 |
| 7,207,961 | B1 * | 4/2007 | Benton | A61F 5/14 602/23 |
| 7,396,338 | B2 * | 7/2008 | Huber | A61F 5/0102 128/893 |
| 7,676,850 | B2 * | 3/2010 | Steel | A43B 7/26 2/239 |
| 8,220,077 | B1 * | 7/2012 | Ott | A41B 11/008 2/239 |
| 8,336,118 | B2 * | 12/2012 | Nordstrom | A41D 31/185 2/115 |
| 8,425,442 | B2 * | 4/2013 | Lundberg | A61F 5/0111 602/27 |
| 8,663,178 | B2 * | 3/2014 | De Luca | A61F 5/019 604/293 |
| 9,248,050 | B2 * | 2/2016 | Cureton | A61F 13/062 |
| 9,320,637 | B2 * | 4/2016 | Amanatullah | A61F 5/0585 |
| 9,421,118 | B2 * | 8/2016 | Cropper | A61F 5/042 |
| 9,492,304 | B2 * | 11/2016 | Fontaine | A61F 5/019 |
| 9,609,896 | B2 * | 4/2017 | Crosby | A43B 13/22 |
| 9,817,440 | B2 | 11/2017 | Longinotti-Buitoni et al. | |
| 9,918,513 | B2 | 3/2018 | Vakili | |
| 9,956,108 | B2 | 5/2018 | Lieberson et al. | |
| 10,045,592 | B2 | 8/2018 | Tozzi et al. | |
| 10,779,578 | B2 * | 9/2020 | Van Tiel | A41B 11/121 |
| 10,993,841 | B2 * | 5/2021 | Riley | A61F 5/0111 |
| 2001/0041855 | A1 * | 11/2001 | Voskuilen | A61F 5/0111 602/65 |
| 2003/0005601 | A1 * | 1/2003 | Kasahara | A43B 7/142 36/88 |
| 2006/0085894 | A1 * | 4/2006 | Yakopson | A61F 13/08 2/239 |
| 2007/0074334 | A1 * | 4/2007 | Steel | A43B 3/105 2/239 |
| 2008/0155731 | A1 * | 7/2008 | Kasahara | D04B 1/265 2/240 |
| 2008/0262403 | A1 * | 10/2008 | Martin | A41D 13/087 602/63 |
| 2010/0168632 | A1 * | 7/2010 | Abbassian | A61F 5/019 602/30 |
| 2010/0249686 | A1 * | 9/2010 | Rushton | A61F 5/019 602/30 |
| 2011/0054368 | A1 * | 3/2011 | Sanders | A61H 1/0266 601/118 |
| 2012/0215147 | A1 * | 8/2012 | Lunnon | A61F 5/019 602/30 |
| 2012/0232453 | A1 * | 9/2012 | Cropper | A61F 5/3715 602/30 |
| 2013/0060181 | A1 * | 3/2013 | Fontaine | A61F 13/064 602/30 |
| 2013/0269211 | A1 * | 10/2013 | Deans | A41B 11/008 36/84 |
| 2013/0276331 | A1 * | 10/2013 | Steel | A43B 7/26 36/94 |
| 2014/0345033 | A1 * | 11/2014 | Chang | A41B 11/005 2/239 |
| 2015/0148875 | A1 * | 5/2015 | Knez | A61F 7/02 607/111 |
| 2015/0230552 | A1 * | 8/2015 | Metcalf | A41D 13/06 2/239 |
| 2015/0359652 | A1 * | 12/2015 | Lee | A61F 13/068 602/30 |
| 2016/0088879 | A1 * | 3/2016 | Salah | A61F 13/064 2/240 |
| 2016/0345659 | A1 * | 12/2016 | Sturgis | A43B 7/26 |
| 2017/0007465 | A1 * | 1/2017 | Edwards | A61F 13/068 |
| 2017/0196513 | A1 * | 7/2017 | Longinotti-Buitoni | H05K 1/0283 |
| 2017/0265527 | A1 * | 9/2017 | Kim | A41B 11/003 |
| 2017/0347723 | A1 * | 12/2017 | Millet | A61F 5/019 |
| 2018/0084839 | A1 * | 3/2018 | Neal | A41B 11/008 |
| 2018/0116853 | A1 * | 5/2018 | Jones | A61F 5/0111 |
| 2018/0184724 | A1 * | 7/2018 | Baker | A41B 11/004 |
| 2018/0317565 | A1 * | 11/2018 | McCuaig | A41B 11/008 |
| 2018/0333285 | A1 * | 11/2018 | Thor | A43B 7/20 |
| 2019/0125195 | A1 * | 5/2019 | Hielscher | A61B 5/24 |
| 2019/0166948 | A1 * | 6/2019 | Scaife | A43B 7/26 |
| 2019/0167462 | A1 * | 6/2019 | Shaffer | A61F 5/019 |
| 2019/0289956 | A1 | 9/2019 | Eugene | |
| 2021/0145079 | A1 * | 5/2021 | De Freitas Silva | A61F 13/066 |

\* cited by examiner

|  | Control | Printed Silicone | | | | | | | Knit Silicone | | |
|---|---|---|---|---|---|---|---|---|---|---|---|
|  |  | Square Outline | | Full Square | | Vertical Lines | | Horizontal Lines | | Course Knit | | |
|  |  | TCS-7772 | TCS-7663 | TCS-7772 | TCS-7663 | TCS-7772 | TCS-7663 | TCS-7772 | TCS-7663 | Single | Double | Triple |
| Avg - Dry Insole | 25 | 30.2 | 28.2 | 28.8 | 31.6 | 26.8 | 29.8 | 27.8 | 27.2 | 28 | 34.8 | 34.8 |
| Avg - Wet Insole | 31.2 | 30.8 | 30.8 | 30 | 28.6 | 29.4 | 30.6 | 30.4 | 30.8 | 24.2 | 33.8 | 33.4 |

FIG. 9G

GRIP ENHANCEMENT AND PROTECTION FOR THE FEET

CROSS REFERENCES TO RELATED APPLICATIONS

This application is related to and claims priority from the following US patents and patent applications. This application is a continuation-in-part of U.S. application Ser. No. 15/927,231, filed Mar. 21, 2018, which claims priority from U.S. Provisional Patent Application No. 62/475,115, filed Mar. 22, 2017, each of which is incorporated herein by reference in its entirety.

BACKGROUND OF THE INVENTION

1. Field of the Invention

The present invention relates to apparatuses and methods for injury prevention. In particular, the subject matter relates to the foot.

2. Description of the Prior Art

Repeated impact and stresses from engaging in activities such as running, walking, and kicking creates considerable risk to the feet. In many activities, equipment is used to provide a level of yield and impact absorbance when the foot of an athlete comes into contact with a surface, but even with this protection, the foot still experiences considerable impact forces. Athletic fields, for example, specifically impart significant stressors on the foot when the ligaments of the toe experience hyperextension. Overstretching, overuse, and overloading of the foot also imparts significant strain to the bottom of the foot, often leading to individuals developing injuries to the plantar fascia.

In events such as football, for example, a common injury known as "turf toe" causes an inability to participate in the game of football and develops with repeated forceful impact with the hard surface of the field. Turf toe is a debilitating injury, typically associated with the hallux, which is caused by a hyperextension of the collateral ligaments on either side of the toe and the flexor halluces brevis under the hallux, most commonly as a result of slipping or high impact with a hard, flat surface such as a (turf) football field. Turf Toe requires a one to three-week recovery time depending on the degree of hyperextension of the ligaments. In attempting to prevent turf toe, it is not uncommon for athletes to heavily wrap their feet in tapes or medical bandages.

In the game of basketball, similar injuries are caused by impact with the hard and often slick surface of the playing floor and by repeated jumping and pushing off movements. Additionally, high velocity impacts with the court or accidental contact often results in toe fractures and turf toe. A toe fracture often causes an athlete to miss four to eight weeks of playing time. In the game of soccer—in addition to the possibilities for the incidence of both turf toe and toe fractures—repetitive impact injuries with a soccer ball often causes foot injuries over time that cause missed time by a player due to such repetitive impact foot injuries.

Specialty footwear has been further designed to address specific challenges in other fields, such as healthcare. For example, graduated compression is often included in socks designed for diabetic patients in order to increase blood flow.

Prior art patent documents include the following:

U.S. Pat. No. 9,248,050 for Wound Dressing Garment by inventor Cureton, et al., filed Oct. 11, 2012, and issued Feb. 2, 2016, is directed to: A wound dressing garment is provided. The wound dressing garment includes a wearable garment including a portion having a hole configured to receive a wound dressing therein in combination with the wound dressing. The wound dressing includes a border connecting the wound dressing to the wear able garment where the border extends around the perimeter of the hole to locate the wound dressing therein. The wound dressing may include one or more additional layers including a hydrogel layer. A method for treating wound or preventing bed sores using the wound dressing garment is also provided.

U.S. Pat. No. 9,421,118 for Digital control strap system and method by inventor Cropper, et al., filed Mar. 9, 2011, and issued Aug. 23, 2016, is directed to: a digital strapping system comprising an alternatively configurable hallux strap system for positioning and exercising a hallux of a foot, and/or an alternatively configurable osteotomy strap system for positioning and exercising a second and/or third digit of a foot.

U.S. Pat. No. 5,928,173 for Turf toe brace by inventor Unruh, filed Dec. 15, 1997, and issued Dec. 27, 1999, is directed to: a turf toe brace includes a flexible boot adapted for snugly anchoring the brace to a foot of a user, an elongate generally non stretchable strap releasably joinable in a multiplicity of configurations to the boot by a fastening mechanism and a toe loop. The toe loop is joined to the strap opposite the boot. In use the strap passes under the foot and is connected to at least one side of the boot in such a manner as to pull downwardly on the great toe and help prevent hyper-extension of the great toe, especially during work or athletic events.

U.S. Pat. No. 9,956,108 for Sock assembly for correcting toe deformation by inventor Lieberson, et al., filed Dec. 7, 2011, and issued May 1, 2018, is directed to: a sock assembly for correcting a deformed toe of a foot of a person, including a sock wearable on an at least a part of the foot, a strap connected to the sock and wearable on an at least a part of the foot and wrappable on an at least a part of the deformed toe as the sock it worn on the foot, consequently applying a corrective force on the deformed toe.

U.S. Pat. No. 9,492,304 for Orthopedic device for mechanical treatment of hallux valgus by inventor Fontaine, et al., filed Mar. 10, 2011, and issued Nov. 15, 2016, is directed to: an orthopedic device is provided for treatment of Hallux Valgus. The orthopedic device includes a main part in the form of an elastic sleeve, intended to exert a restraining force locally on the metatarsals, a distal part for encapsulating the big toe, and a connecting band between the main part and the distal part, intended to be tensioned in order to exert a lateral force on the big toe that is directed inwards in relation to the axis A of the human body. A pad is secured to the inner wall of the device, creating a localized increased thickness, and arranged to be positioned against the first metatarsal of the big toe. The pad acts as an anchor during the application of the lateral force, in different positions of the foot, thus allowing the tensile force on the connecting band to be adjusted. The combined restraining and lateral forces serve to re-align the joint during walking.

U.S. Pat. No. 7,676,850 for Toe spacer sock and corrective footwear by inventor Steel, filed Apr. 3, 2006, and issued Mar. 16, 2010, is directed to: a sock contains built-in cushions or spacers to correct or protect the toes, or to provide the wearer better comfort. The cushions or spacers may be retained between the toes in a tube, formed integrally with the sock, which is everted to a position between adjacent toes. A strap may also be built into the Sock, or into a shoe, shoe insert, boot, Sandal or slipper to maintain a corrective force on the great toe.

U.S. Pat. No. 8,663,178 for Reinforced stocking or sock for the prevention and/or treatment of hallux valgus by inventor De Luca, filed Feb. 19, 2008, and issued Mar. 4, 2014, is directed to: a stocking or sock with a foot portion includes a pocket for containing the big toe that is separate from the pocket(s) for the other toes. At least one medial reinforcement, integrally attached to the foot portion, entirely or partially surrounds the big toe pocket, while the medial part of the foot portion, and the posterior part or heel of the foot portion are anchored to the posterolateral or lateral part of foot portion, coming to bear on the anterior part of said pocket, counteracting any lateral deflections, and on the medial part, corresponding to the metatarsophalangeal joint and the first metatarsal of the foot, counteracting any medial deflections.

U.S. Pat. No. 9,918,513 for Reversible protective footwear by inventor Vakili, filed Mar. 12, 2014, and issued Mar. 20, 2018, is directed to: protective footwear comprising a flexible strap that can be wrapped around a bare foot in order to provide protection and traction to the ball and heel of the foot. The footwear can provide protection from rough or hot surfaces, for example swimming pool decks or hot sand at the beach. The footwear can also provide traction for the user on wet or slippery surfaces. The footwear is designed to minimally cover the foot, giving the user a "barefoot" feeling, while still providing protection and traction to the pressure points (e.g., ball and heel) of the foot. The footwear can be securely fastened to the user's foot such that it does not fall off during routine physical activity (e.g., swimming, walking, etc.).

US Publication No. 2016/0088879 for Health care sock by inventor Salah, filed Sep. 30, 2015, and published Mar. 31, 2016, is directed to: a health care sock having an interior cavity for receiving a human foot through an opening portion, comprising an outer layer conforming to the shape of the foot, a toe portion, a heel portion and a base adjacent to the outer layer and conforms to the sole of the foot in order for the sole to rest onto the base.

U.S. Pat. No. 10,045,592 for Toe protector for athletic footwear having removable cleats by inventor Tozzi, et al., filed Aug. 5, 2014, and issued Aug. 14, 2018, is directed to: a toe protector adapted to be removably attached to an external portion of the toe-box of cleated athletic footwear having removable cleats to protect an athlete's foot from crush injuries. The toe protector includes plantar flanges, each having at least one threaded cleat stud receiving hole used to attach the toe protector to the cleated athletic footwear in an external relationship. It is formed plastic, polycarbonate, or other materials, having sufficient thickness and hardness to withstand deformation and deflect crush forces applied to the toe-box of the cleated athletic footwear. It is designed to be universally applicable to most all athletic footwear having removable cleats available from known manufacturers and can be easily transferable to other similarly sized cleated footwear.

U.S. Pat. No. 9,817,440 for Garments having stretchable and conductive ink by inventor Longinotti-Buitoni, et al., filed Jul. 14, 2015, and issued Nov. 14, 2017, is directed to: methods of forming garments having one or more stretchable conductive ink patterns. Described herein are method of making garments (including compression garments) having one or more highly stretchable conductive ink pattern formed of a composite of an insulative adhesive, a conductive ink, and an intermediate gradient zone between the adhesive and conductive ink. The conductive ink typically includes between about 40-60% conductive particles, between about 30-50% binder; between about 3-7% solvent; and between about 3-7% thickener. The stretchable conductive ink patterns may be stretched more than twice their length without breaking or rupturing.

SUMMARY OF THE INVENTION

The present invention relates to apparatuses and methods for injury prevention. In particular, the subject matter relates to the foot. In one embodiment, the invention is directed to the prevention of turf toe of the hallux. In another embodiment, the present invention is constructed for use with other areas of the foot, as well as other limbs, including the legs, forearms, and hands.

It is an object of this invention to employ specific components to provide a footwear object that is comfortable, unobtrusive, improves the grip of a user, and reduces likelihood of common podiatric injuries such as turf toe and toe fractures.

In one embodiment, the present invention is directed to: a footwear article, comprising: a textile structure including a toe region, an arch region, a heel region, and an ankle region; a toe strap, wherein the toe strap is integrated within the textile structure, and wherein the toe strap is constructed with a material that is more inelastic than the textile structure; at least one external grip element; and at least two compression areas; wherein the toe region includes two toe compartments; wherein the toe strap extends from the heel region to the toe region, and wherein the toe strap further extends from a bottom of one of the two toe compartments to a top of the one of the two toe compartments; wherein the at least one external grip element is integrated within a bottom of the textile structure; and wherein the at least two compression areas are located on the arch region and on the ankle region.

In another embodiment, the present invention is directed to: a footwear article, comprising: a textile structure including a toe region, an arch region, a heel region, and an ankle region; at least one toe strap integrated into the textile structure, wherein the at least one toe strap is constructed with a material that is more inelastic than the textile structure; at least one external grip element; and at least two compression areas; wherein the toe region includes at least two toe compartments; wherein the at least one toe strap includes a continuous band of material which extends from the heel region to the toe region, and wherein the at least one toe strap further extends from a bottom of one of the at least two toe compartments to a top of the one of the at least two toe compartments; wherein the at least one toe strap applies tension in a direction toward a bottom of the footwear article and a rear of the footwear article; and wherein the at least two compression areas are located on the arch region and on the ankle region.

In yet another embodiment, the present invention is directed to: a footwear article, comprising: a textile structure including a toe region, an arch region, a heel region, and an ankle region, wherein the toe region includes at least two toe compartments; least two compression areas; and at least one toe strap, internal grip elements, or at least one integrated external grip element; wherein the at least one strap is constructed with a material that is more inelastic than the textile structure; wherein a first of the at least two compression areas is located on the arch region and a second of the at least two compression areas is located on the ankle region; wherein the textile structure, the at least one toe strap, and the at least two compression areas are knitted or woven; and wherein the at least two compression areas encircle the footwear article.

These and other aspects of the present invention will become apparent to those skilled in the art after a reading of the following description of the preferred embodiment when considered with the drawings, as they support the claimed invention.

BRIEF DESCRIPTION OF THE DRAWINGS

FIG. 9G is a table illustrating angles of impending motion for several samples of a footwear object according to one embodiment of the present invention.

DETAILED DESCRIPTION

Figure 1:
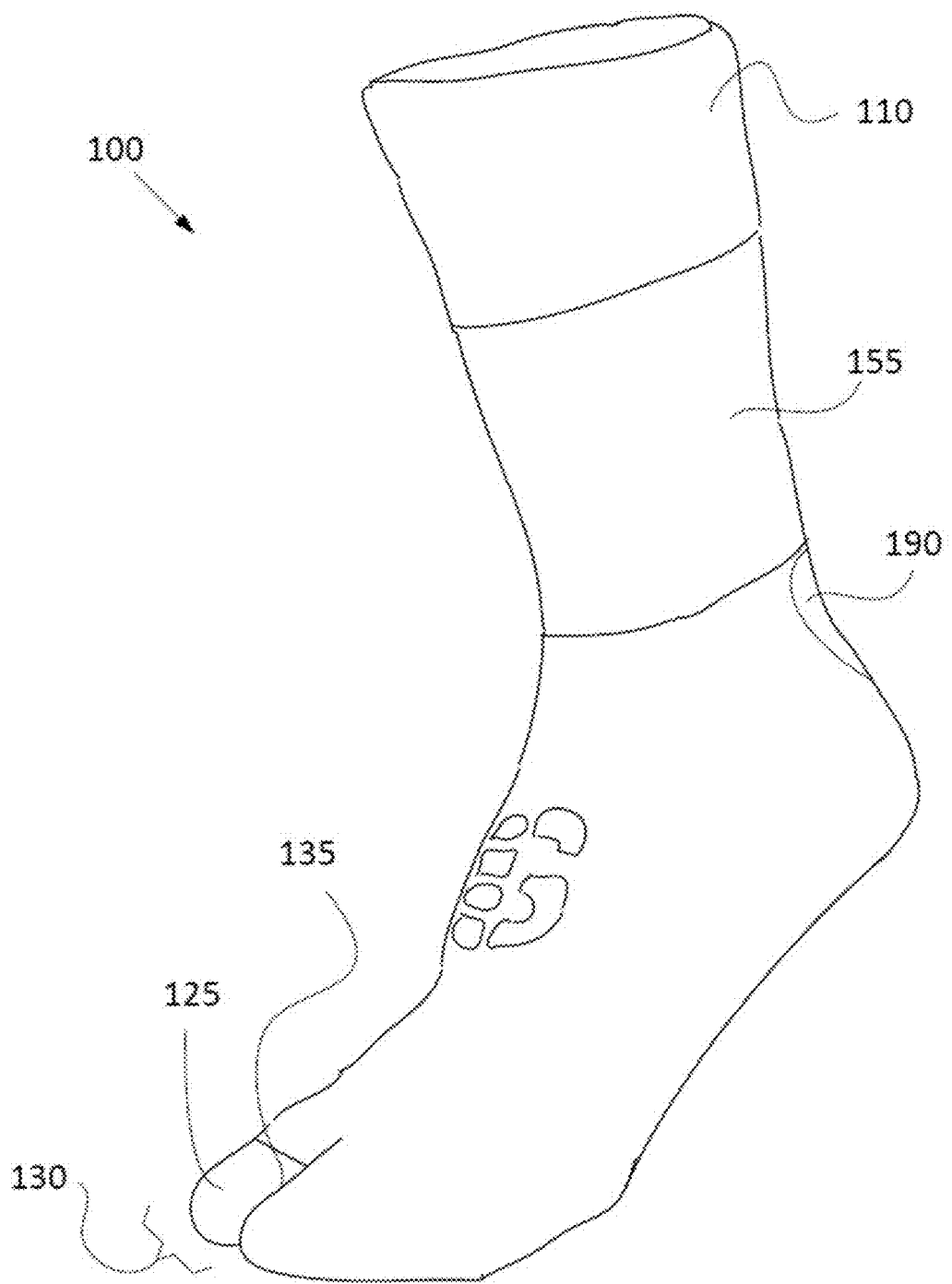
FIG. 1 illustrates a front perspective view of a footwear object according to one embodiment of the present invention.

The present invention is generally directed to footwear articles for athletic performance. The articles include a combination of layers, components, and compartments that advantageously provide structure, support, and increased performance for a user while maintaining comfortability.

In one embodiment, the present invention is directed to: a footwear article, comprising: a textile structure including a toe region, an arch region, a heel region, and an ankle region; a toe strap, wherein the toe strap is integrated within the textile structure, and wherein the toe strap is constructed with a material that is more inelastic than the textile structure; at least one external grip element; and at least two compression areas; wherein the toe region includes two toe compartments; wherein the toe strap extends from the heel region to the toe region, and wherein the toe strap further extends from a bottom of one of the two toe compartments to a top of the one of the two toe compartments; wherein the at least one external grip element is integrated within a bottom of the textile structure; and wherein the at least two compression areas are located on the arch region and on the ankle region.

In another embodiment, the present invention is directed to: a footwear article, comprising: a textile structure including a toe region, an arch region, a heel region, and an ankle region; at least one toe strap integrated into the textile structure, wherein the at least one toe strap is constructed with a material that is more inelastic than the textile structure; at least one external grip element; and at least two compression areas; wherein the toe region includes at least two toe compartments; wherein the at least one toe strap includes a continuous band of material which extends from the heel region to the toe region, and wherein the at least one toe strap further extends from a bottom of one of the at least two toe compartments to a top of the one of the at least two toe compartments; wherein the at least one toe strap applies tension in a direction toward a bottom of the footwear article and a rear of the footwear article; and wherein the at least two compression areas are located on the arch region and on the ankle region.

In yet another embodiment, the present invention is directed to: a footwear article, comprising: a textile structure including a toe region, an arch region, a heel region, and an ankle region, wherein the toe region includes at least two toe compartments; least two compression areas; and at least one toe strap, internal grip elements, or at least one integrated external grip element; wherein the at least one strap is constructed with a material that is more inelastic than the textile structure; wherein a first of the at least two compression areas is located on the arch region and a second of the at least two compression areas is located on the ankle region; wherein the textile structure, the at least one toe strap, and the at least two compression areas are knitted or woven; and wherein the at least two compression areas encircle the footwear article.

None of the prior art discloses the combination of a footwear article with one or more layers, toe straps, compressive zones, and grip zones.

In one embodiment, the present invention is directed to a footwear object capable of protecting the feet and preventing many common injuries, such as Turf Toe, that result from repeated impact and stress that is common athletic events such as football, soccer, basketball, or baseball. In one embodiment, the present invention prevents turf toe by limiting a range of motion of the hallux to minimize risk of hyperextension and further provides compressive support and increased grip to maximize athletic performance.

The footwear object is, in one embodiment, designed to fit snugly around a foot and provide compressive support to the toes, ankle, and bottom of the foot. This fit and compressive support is specifically designed to prevent any toe from moving beyond its normal range of motion. In one embodiment, this is accomplished by providing a toe strap and toe partition, isolating the toe the wearer wishes to protect, as the toe protection mechanism. The footwear object is further designed to disperse weight evenly over the entire foot, helping to reduce the amount of strain concentrated on the toes. The footwear object further includes, in another embodiment, an enhanced grip element between the footwear object and any shoe that is worn over the footwear object. This element prevents slippage of the foot within the shoe and minimizes the chance that weight will be concentrated on the toes as the toes impact the front inside surface of a shoe. In another embodiment, the footwear object also has an ankle support which, in on embodiment, is implemented as a cross-ankle strap that assists in stabilizing the ankle of the wearer.

In another embodiment of the current invention, a footwear object, such as an athletic sock, stocking, or specialty sock, includes a toe support mechanism and an ankle support mechanism, wherein the toe support mechanism further comprises a toe strap configured to protect at least one toe, wherein the toe strap extends beneath the arch of the footwear object to provide connected toe and arch support. The footwear object is adapted to prevent or reduce the severity of turf toe injuries and arch injuries to a foot. The footwear object having a toe support mechanism comprises at least one toe partition (e.g., at least two compartments) and a toe strap, where the toe support mechanism is adapted to support toe ligaments, prevent the full weight of the foot from concentrating on the toes, and position the toes to maintain function and prevent injury. Additionally, the support and protective portions of the footwear object are incorporated as knitted portions, layered portions applied over the knitted structure, or are incorporated as multiple knitted layers with or without the inclusion of layered portions, wherein the article provides grip, compression, and impact protection for the foot and ankle of a user.

Referring now to the drawings in general, the illustrations are for the purpose of describing one or more preferred embodiments of the invention and are not intended to limit the invention thereto.

FIG. 1 presents a perspective view of a left-foot footwear object 100 consistent with certain embodiments of the present invention. In a non-limiting example, a left sock 110 fitting a left foot and having a knitted and/or woven material base consistent with certain embodiments of the present invention is shown. In one embodiment, an interior toe divider 135 creates a toe partition 130 for a hallux 905. In another embodiment, the interior toe divider 135 is constructed to create a compartment to receive any toe or combination of toes. For example, in one embodiment, the compartment is constructed to receive a hallux and a second toe. FIG. 1 further illustrates a toe strap 125, which wraps up over the front of the hallux 905 and terminates at a position on top of the hallux to prevent hyperextension of the hallux. In another embodiment, the footwear object 100 is constructed for a left foot or a right foot, wherein a right foot construction is a mirror of the left foot construction.

In a non-limiting example, an ankle support 155 is illustrated encircling the lower leg just above the ankle. In alternative embodiments, the ankle support 155 extends from well below the ankle to a point at the top of the footwear object. In another embodiment, the ankle support 155 is multiple rings encircling the lower leg at various levels. In addition, a padded zone 190 is illustrated covering the area of the Achilles tendon at a rear of the sock 110. In another embodiment, a padded zone 190 extends from the bottom of the footwear object to the top of the footwear object, In a further embodiment, the padded zone 190 extends from well below the Achilles tendon to any point above the Achilles tendon along the back of the sock.

In an exemplary embodiment, the footwear object 100 is designed to protect the feet of the wearer while providing support for the toes, arches, and ankles of the wearer. The footwear object 100 provides toe flexibility, compression, breathability, wicking factor, grip, hand feel/comfort, and abrasion as set forth in the deflection, Martindale abrasion test and Gravimetric Absorbency Testing System (GATS) test, as well as the look and feel that is important to a wearer. When verifying the footwear object with the Martindale abrasion test, footwear object does not develop holes or experience thinning when tested using up to 30,000 cycles at a pressure between 7 KPa-13 KPa. The footwear object also has an air permeability in grip regions of at least 100 ft$^3$/min/ft$^2$. Results of a Frazier Air Permeability Test comparing the different methods of applying the gripping elements of the present invention are shown in Table 1 below.

| Silicone | Printed Lines | Printed Outline | Printed Square | Single Course | Double Course | Triple Course |
| --- | --- | --- | --- | --- | --- | --- |
| 1 | 142 | 153 | 13 | 154 | 176 | 203 |
| 2 | 138 | 151 | 16 | 153 | 174 | 200 |
| 3 | 141 | 150 | 15 | 157 | 173 | 201 |
| 4 | 144 | 144 | 15 | 153 | 176 | 203 |
| 5 | 139 | 151 | 16 | 153 | 179 | 205 |
| Average | 140.8 | 149.8 | 15 | 154 | 175.6 | 202.4 |

Table 1 illustrates Frazier Air Permeability Test results comparing different methods of applying the gripping elements of the present invention (Silicone) to footwear objects, where the air permeability (in ft$^3$/min/ft$^2$) was measured for the grip enhancing area of the footwear object.

The footwear object is constructed from a woven or knitted fabric composed of any of a plurality of yarns, threads, or unwoven materials. Materials used in the manufacture of the footwear object 100 include artificial fibers such as, but not limited to, nylon, nylon 6, nylon 66, rayon, polyester (such as SORBTEK), spandex, or silicone, natural fibers, such as cotton, wool, merino wool, linen, silk, or any other natural or synthetic fibers, blends of these fibers, and/or combinations of these fibers. Materials are selected in part due to their ability to provide compression in selected regions of the footwear object. In another embodiment, the materials provide compression throughout the entire footwear object.

In one embodiment, the footwear object 100 improves on the performance of existing technologies such as toe braces, diabetic socks, and grip socks by incorporating multiple functions into a single footwear object and operating to prevent injuries through the inclusion of a novel, non-obvious combination of components, such as a heel pad and toe spacer support. In one embodiment, the footwear object 100 comprises a covering for the entire foot and ankle of a wearer. Additionally, the interior toe divider 135 provides for separation between any one or all toes to reduce impact injuries and provide greater support for the wearer. In a non-limiting example, the hallux is separated from the rest of the toes to reduce impact injuries to the hallux, which suffers from a greater incidence of injury based upon the relative size of the hallux and its importance in maintaining balance and use of the foot in sports activities.

Figure 2:
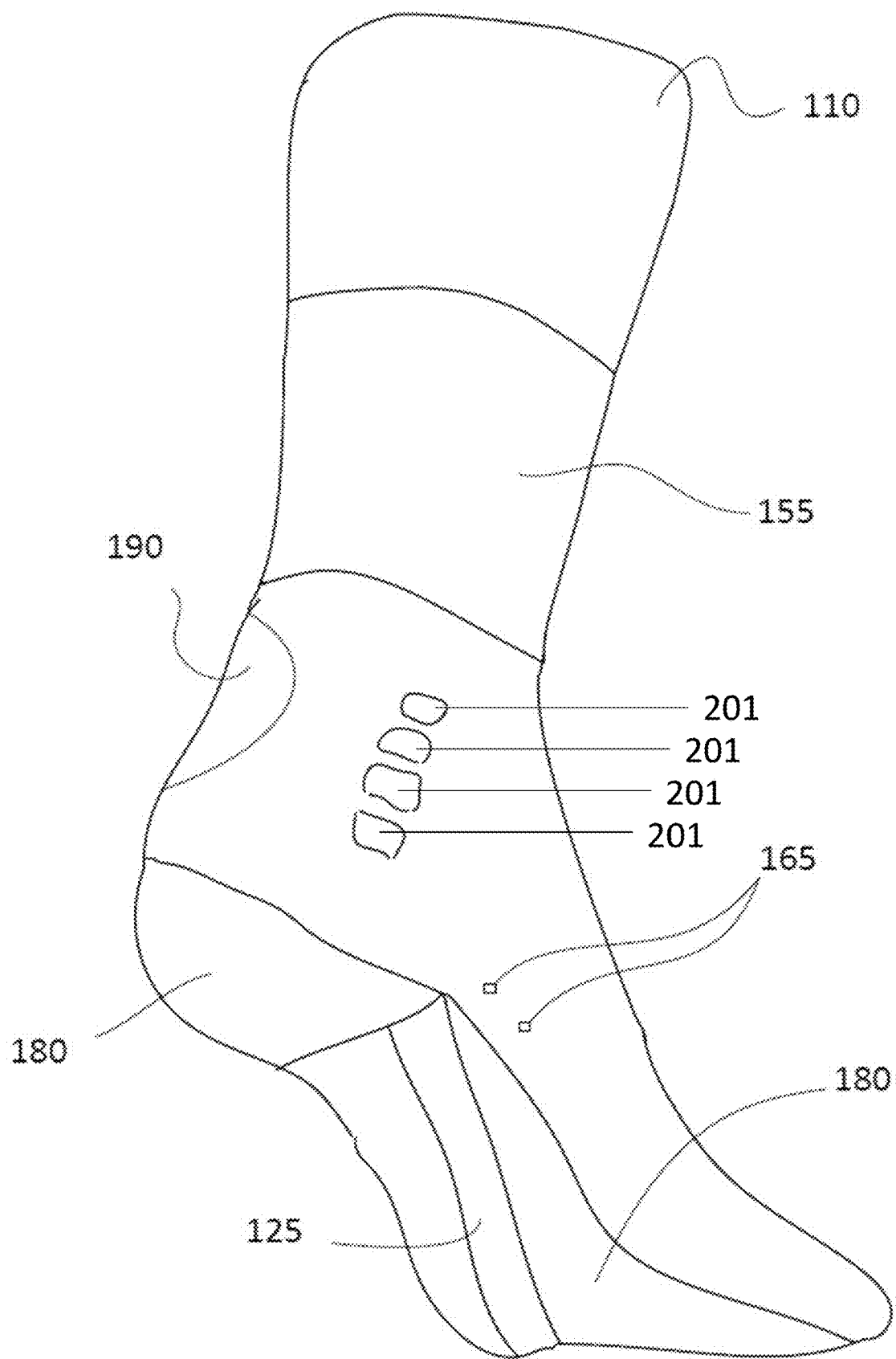
FIG. 2 illustrates a rear perspective view of a footwear object having a woven and/or knitted material base according to one embodiment of the present invention.

FIG. 2 illustrates a side perspective view of a right-foot footwear object according to one embodiment of the present invention. The footwear object is a textile foot covering 110 consistent with fitting a right foot is shown. The foot is lifted slightly to show the underside of the sock 110. The ankle support 155 encircles the lower leg and the padded zone 190 is seen at the back of the foot. In one embodiment, sensors 201 are illustrated on the outside of the footwear object.

The toe strap 125 extends from the top of the hallux (not visible in this view since it is located on the far side of the foot) by emerging from under the hallux and crossing the bottom of the foot, pressing against the arch of the foot, and terminating in front of the heel.

In the illustrated embodiment, two of the one or more grip pads 180 are located on the underside of the sock 110; one is located at the back of the foot under the heel and another is located at the front of the foot in front of the toe strap 125.

In an embodiment, the footwear object 100 includes preventative support elements to keep a wearer from harm to the ankle or foot. The elements include, in one embodiment, a ribbed ankle structure 155, a padded zone 190, the one or more grip pads 180 on the heel pad, formed from compression fabric, a knitted silicone grip on the outside surface of the bottom of the footwear object 100, and the one or more grip pads 180 under the toes to provide support and protection for the toes of the wearer. In one embodiment, the padded zone 190 is a densely knitted portion at the back of the ankle above the heel to prevent blisters. In an exemplary embodiment, the footwear object 100 provides a complete cover for the foot and ankle of the wearer to provide support and protection against injury to the wearer's foot and ankle. The foot portion of the footwear object 100 has a compressive spandex knitted fabric on the top dorsal portion of a wearer's foot. The foot portion also includes compressive spandex inlaid in the knit of the fabric that forms the bottom portion and that covers the bottom of the wearer's foot. In one embodiment, the spandex is 150 denier or 280 denier spandex yarn.

When referring to a compression layer of the footwear object, this refers to increased tension, a tension creating design, additional elastic, increased materials in a given area or even a reduction of materials. In one embodiment, the footwear object creates levels of graduated compression in order to increase blood flow of the user. This compression is also operable to include thermal reactive yarns that contain antimicrobial properties and infrared reflective technology to create one or more layers of compression base layer materials. In a preferred embodiment, the thermal reactive fiber is a polymer with quartz, silicon oxide and titanium oxide particles, such as CELLIANT. These yarns and the compression action of these materials when woven into cloth-like coverings help stabilize toe ligaments, increase circulation, wick sweat, prevent microbial growth, increase grip strength, and return energy back to the cells of the user's skin. The compression base layer material and/or stabilizing material adds additional support to the toe ligaments to help stabilize them and reduce the likelihood of an injury. When formed into a material layer, the compression base layer is seamless so there are no weak or uneven areas.

In one embodiment, the footwear object 100 has a spacer fabric ankle pad that comprises the ankle portion of the footwear object 100. Each portion of the footwear object 100 is composed of multiple layers of fabric types. In a non-limiting example, the inside layer of the footwear object 100 (the portion that comes into contact with the skin of the wearer's foot and ankle) is composed of polyester, a middle layer is composed of wool, and the outside portion is composed of cotton fabric.

In another embodiment, the footwear object 100 includes one or more sensors and/or one or more microchips 165. Sensors are further described in referenced to FIGS. 11A-13C.

Figure 3A:
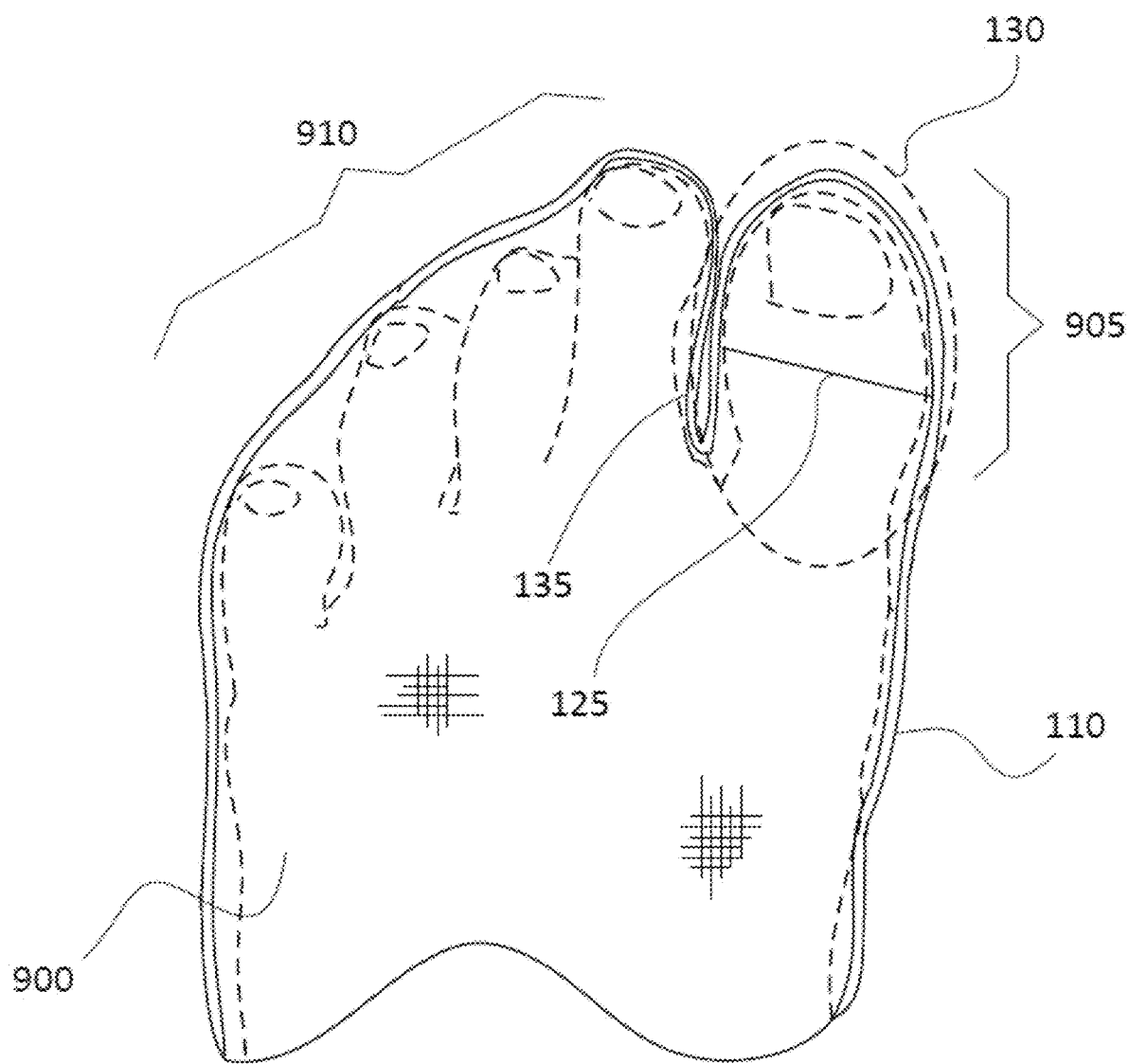
FIG. 3A illustrates a detail view of a footwear object having a woven and/or knitted material base according to one embodiment of the present invention.

FIG. 3A presents a top view of a footwear according to one embodiment of the present invention. The footwear object 110 illustrated is a left-foot embodiment. In a non-limiting example, the toe partition 130 is configured solely to separate the hallux 905 and is formed by the interior toe divider 135. In another embodiment, other toes or other groups of toes are separated by one or more toe partitions. In one non-limiting example, the toe partition is configured with an end portion of the toe strap 125 that forms a cupping section fitting over the hallux so as to entirely protect the hallux and continuing from the base of the toe, under the arch of a user's foot and the distal end of the toe strap 125 being fastened to the portion of the sock 110 associated with the user's heel. In this non-limiting example, all other toes 910 on the foot 900 reside in a non-partitioned area of the sock 110. The toe strap 125 extends up the front of the toe partition 130 and then continues to the rear, terminating on top of the hallux 905. In one embodiment, after wrapping from the bottom to the top of the toe partition 130, the toe strap 125 terminates between 0.25 inches and 2 inches (6.35 millimeters and 50.8 millimeters) from the front of the footwear object. In another embodiment, the toe strap 125 terminates between 0.5 inches and 1.5 inches (12.7 millimeters and 38.1 millimeters) from the front of the footwear object. In additional non-limiting examples, the proximal portion of the toe strap 125 forms a cup section covering one or more toes, these one or more toes separated from the other toes of a user with one or more interior toe divider portions 135, and have a distal portion continuing to the rear of the foot and terminating on the side of the foot close to the heel portion of the footwear object. In another example, the toe partition 135 is a panel that resides inside the sock to separate two or more given toes. In yet another example, the toe partition 135 is formed by joining the top of the sock with the bottom of the sock, creating a partition that separates two or more given toes.

Figure 3B:
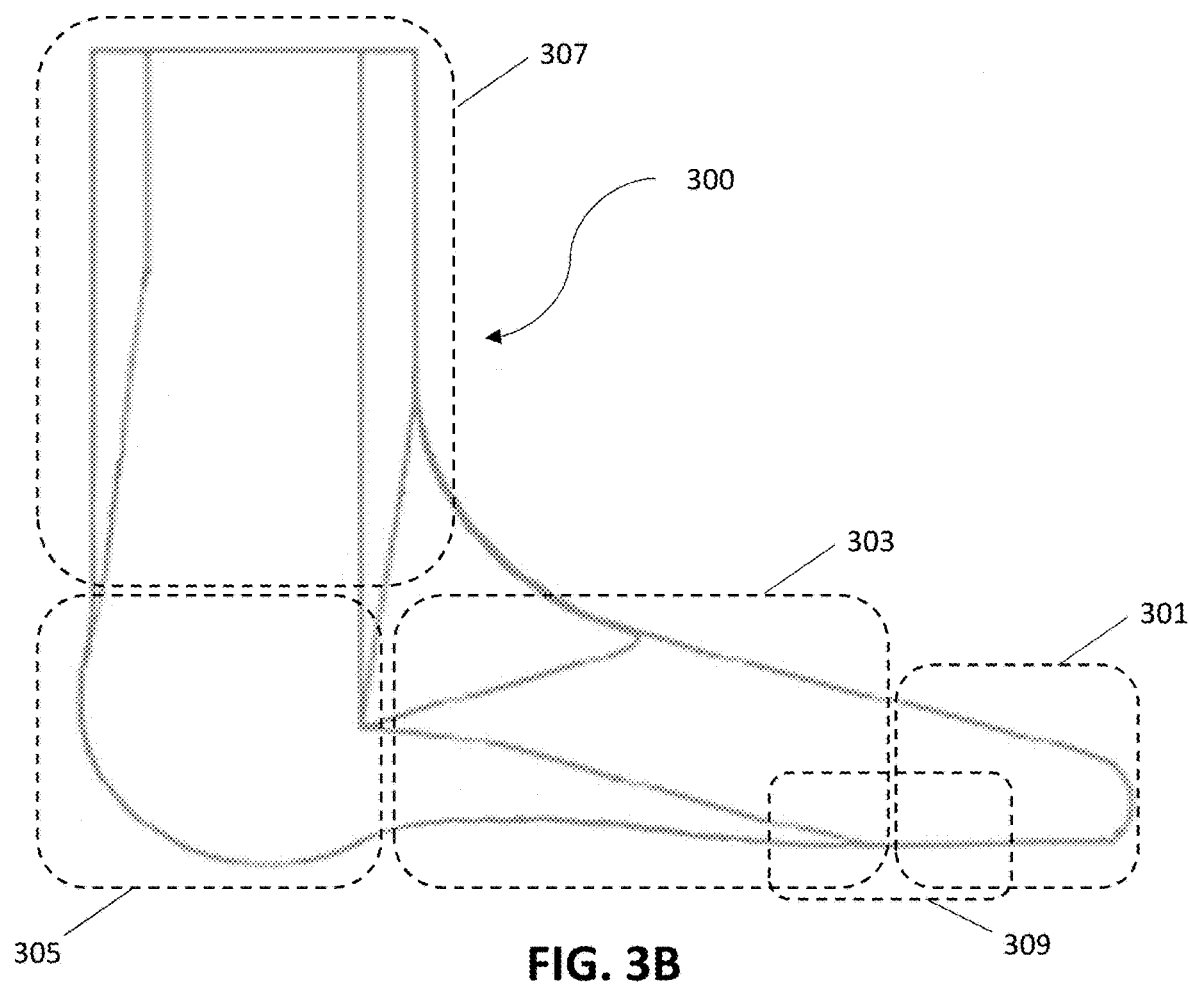
FIG. 3B illustrates a side view of a footwear object highlighting different regions according to one embodiment of the present invention.
Figure 3C:
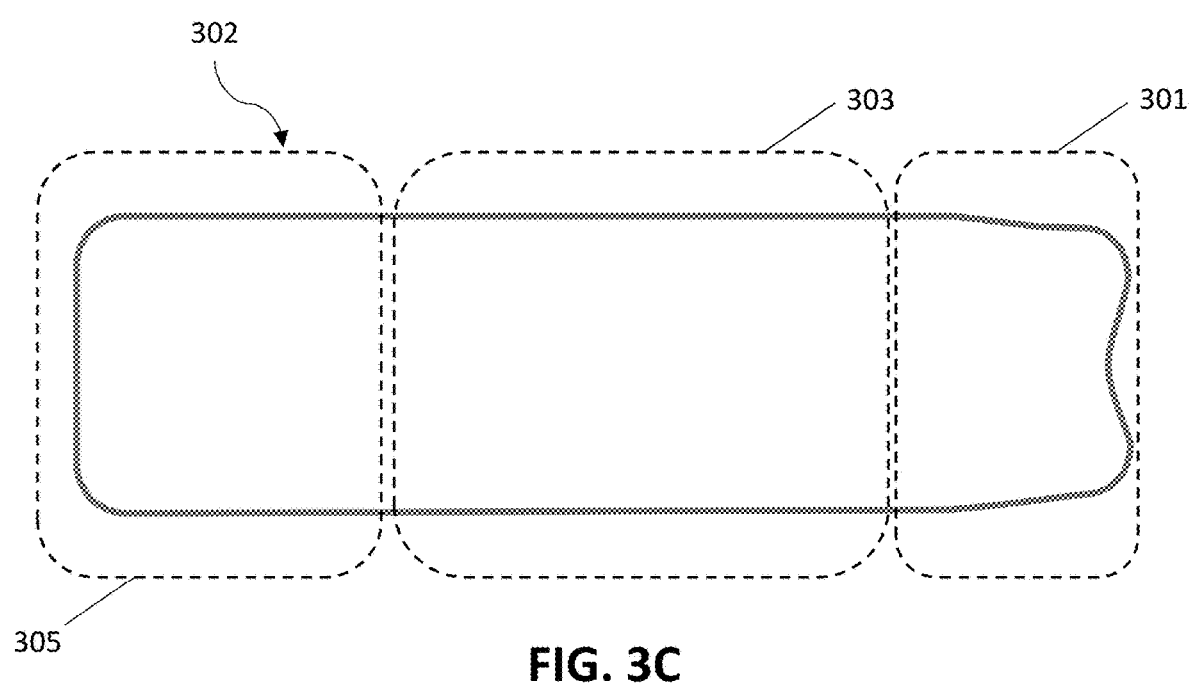
FIG. 3C illustrates a bottom view of a footwear object highlighting different regions according to one embodiment of the present invention.

FIGS. 3B and 3C illustrate views of a footwear object with at least four different regions according to one embodiment of the present invention. FIG. 3B illustrates the side of a footwear object 300 with four different zones, including a toe region 301, an arch region 303, a heel region 305, and a calf region 307. FIG. 3C illustrates the bottom of a footwear object 302, where three regions are visible, including a toe region 301, an arch region 303, and a heel region 305.

Figure 4:
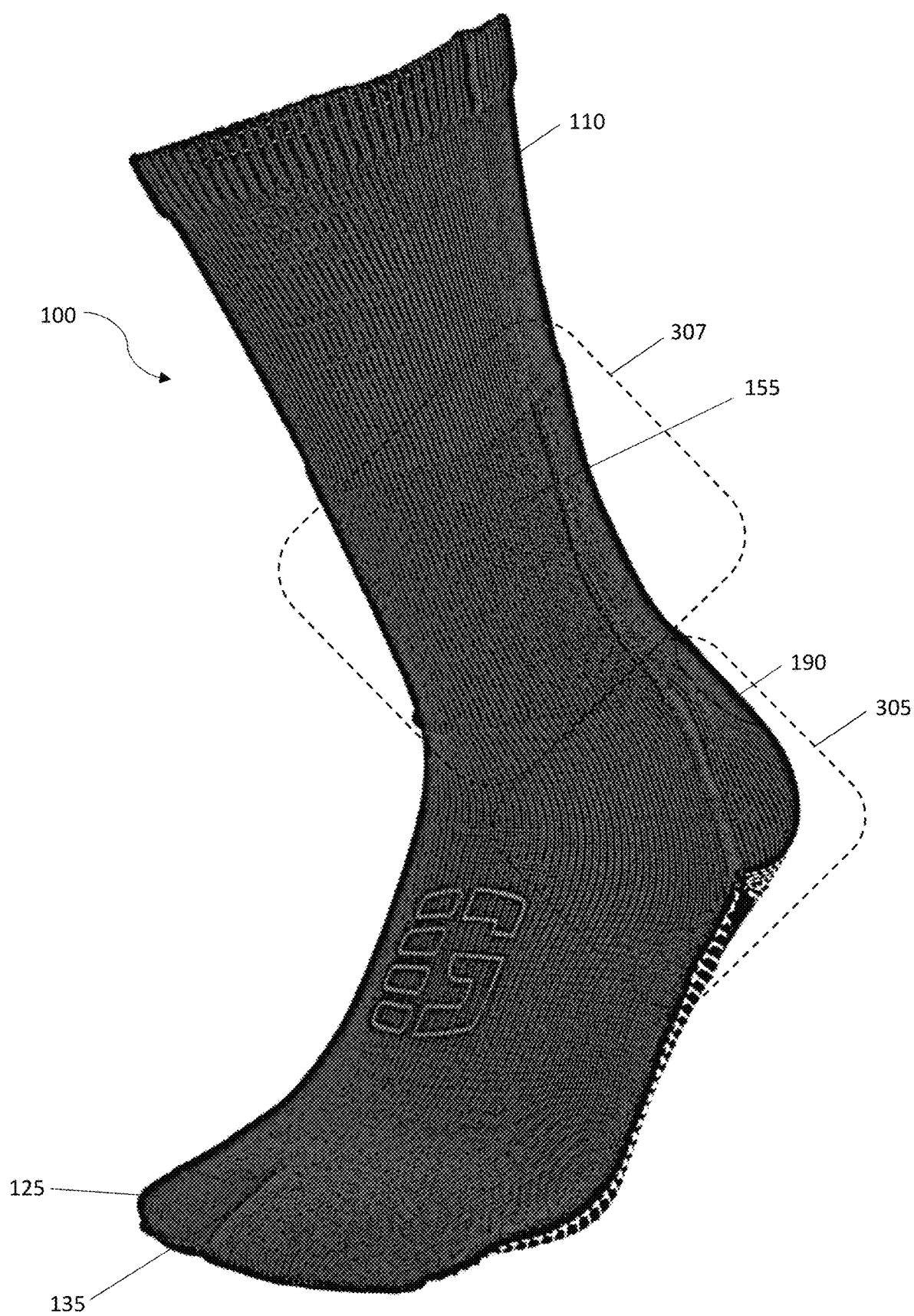
FIG. 4 illustrates a front perspective view of a footwear object, according to one embodiment of the present invention.

FIG. 4 illustrates front view of a knit embodiment of the footwear object described in FIG. 1. In the illustrated embodiment, multiple components of the footwear object injury prevention device 100 are visible, including the distal portion of the toe strap 125, which is wrapped in front of and on top of the hallux. In an alternative embodiment, the toe strap 125 is constructed on or within any compartment, such as a compartment for a second toe, a compartment for a group of toes. In a further embodiment, the footwear object 100 includes multiple toe straps 125 for one or more compartments. For example, in one embodiment, a toe strap 125 is attached to a hallux compartment and a second toe strap 125 is attached to a pinky toe compartment. In another embodiment, a first toe strap 125 is attached to a hallux compartment with a first angle, and a second toe strap 125 is attached to the hallux compartment with a second angle. The hallux compartment is constructed to separate a hallux of a user from the other toes via an interior toe divider portion 135. Also visible is the padded zone 190, which covers from low on the sock to below the ankle support 155, and is operable to cover from below the Achilles tendon area of a user to slightly above the Achilles tendon area of a user, along the back of the sock. The padded zone 190 is a densely knitted portion at the back of the ankle above the heel to prevent blisters. Finally, an ankle support 155 is illustrated encircling the lower leg for a portion of the sock. The angle guard is operable to cover a lower leg of the footwear object between the heel region 305 and a calf region 307 (e.g., from approximately a ball of the foot of a user to the bottom of the calf of a user, or some distance in between during use). In one embodiment, the ankle support 155 is the same thickness as the main body of the footwear object and extends between 0.4 inches and 6.3 inches (10 mm and 160 mm) along the heel region 305 and/or the calf region 307. In another embodiment, ankle support 155 is between 0 inches and 0.2 inches (0 mm and 5 mm) thicker than the main body of the footwear object and is between 1.97 inches and 3.94 inches (50 mm and 100 mm) tall.

Figure 5:
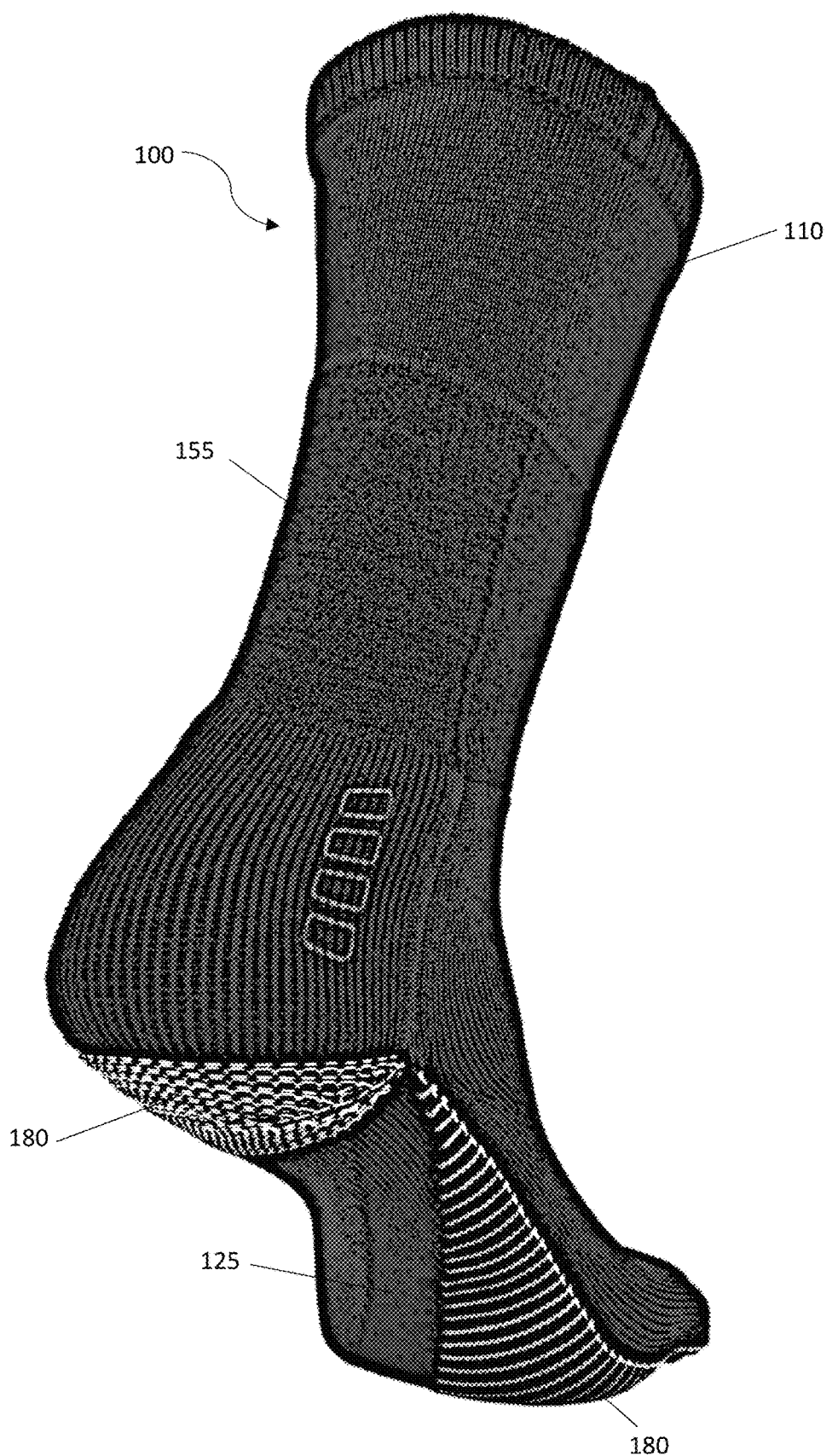
FIG. 5 illustrates a rear perspective view of a footwear object, according to one embodiment of the present invention.

FIG. 5 illustrates a rear view of a knit embodiment of the footwear object described in FIG. 2. FIG. 5 illustrates grip pads 180, which provide support and protection for the toes of the wearer as well as stability for a contained foot, wherein the grip pads 180 are formed from silicone and are knitted onto the outside surface of the bottom of the footwear object. In another embodiment, the grip pads 180 are folds, pleats, or stacked layers of a base material of the footwear object, wherein the folds, pleats, or stacked layers are knitted, woven, adhered, or otherwise attached together or to the footwear object. In an alternative embodiment, a treatment is applied to the fabric of which the footwear object is constructed to provide for greater grip or adhesion characteristics for the footwear object when the footwear object comes into contact with a shoe or flat surface exterior to the footwear object. In another embodiment, the footwear object is be knitted, sewn, or constructed as a layered product having a grip pad forming a gripping bottom surface. Equally desirable, the grip or adhesion property of the footwear object fosters increased grip between the foot of a wearer and the footwear object to maintain contact and position of the foot within the footwear object.

Figure 6A:
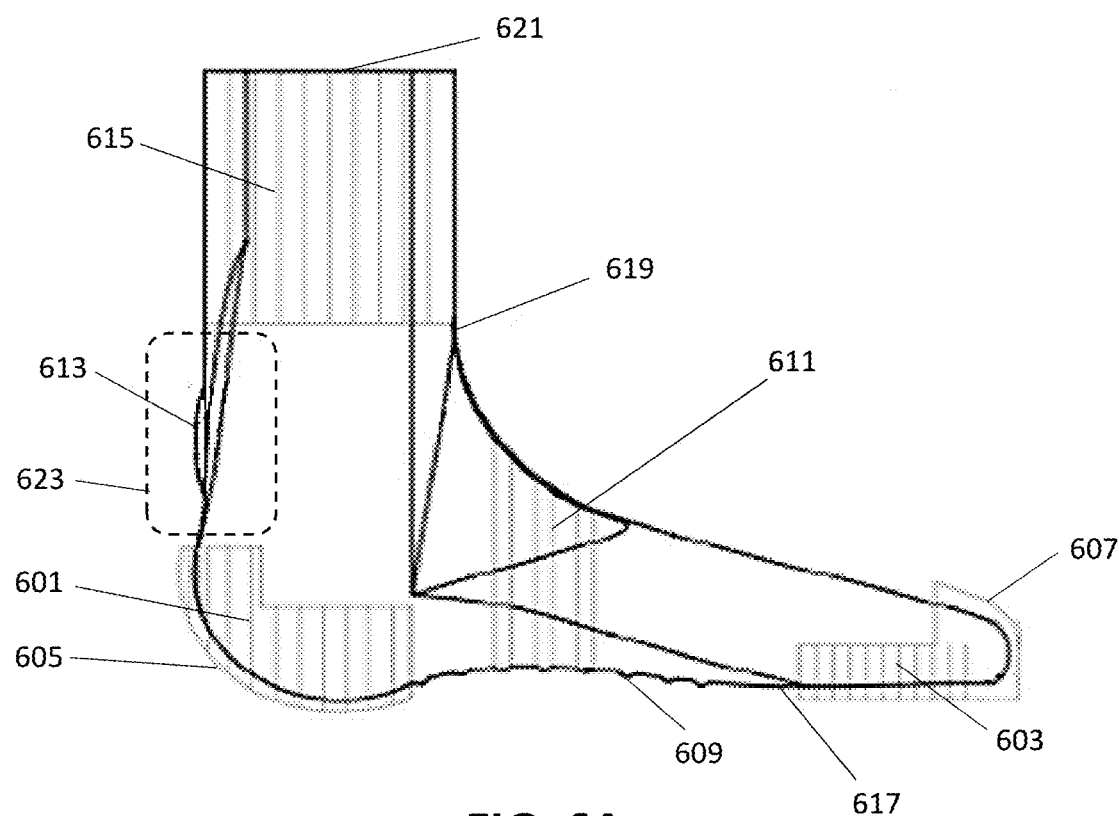
FIG. 6A illustrates a side view of a footwear object including compression zones, according to one embodiment of the present invention.

FIG. 6A illustrates another embodiment of a footwear object which includes multiple compression zones. Compression in the extremities is beneficial for increasing blood flow and maintaining healthy extremities. In this embodiment, the footwear object includes both compressive arch support 611 and ankle support 615. The arch support 611 encircles the middle of the sock, and is operable to provide pressure around the arch of a user's foot. Arch support 611 is knitted or woven in one or more layers from the same materials as the remainder of the footwear object. In another embodiment, different materials are used, with multiple layers present. The fabric layers of the arch support 611 are comprised of artificial fibers such as, but not limited to, nylon, nylon 6, nylon 66, rayon, polyester, spandex, silicone, and others, or natural fibers such as cotton, wool, merino wool, linen, silk, or still other types of natural and synthetic fibers, and fabrics that are blends and combinations of these fibers. In one embodiment, the selected fibers are resistant to deterioration by exposure to perspiration. In a similar manner, the ankle support 615 is operable to cover the lower leg from approximately the ball of the foot 617 of a user to the bottom of the calf of a user 619 or extends from approximately the ball of the foot 617 to any point between the ball of the foot 617 to the bottom of the calf of a user 619. In one embodiment, the ankle support 615 extends to the top of the footwear object 621. In another embodiment, the footwear object includes a base layer or any other material that extends between the ankle support 615 and the top of the footwear object 621. The ankle support 615 is designed to encircle the ankle portion of the user's foot from below the ankle to high on the user's leg so as to protect the entirety of a user's ankle and guard against conditions such as high ankle sprains and other leg injuries associated with the ankle. The ankle support mechanism encircles the ankle with a cylindrical structure, a cross-shaped structure, rings, vertical strips, horizontal strips, waves, patterns, or any other structure that encircles the ankle and provides the protection and support required of this portion of the user's leg. The ankle support mechanism 615 comprises a compressive material woven into the footwear object or applied over the fabric of the footwear object. In a non-limiting example, the compressive material is neoprene, spandex, nylon, cotton, polypropylene, rayon, wool, merino wool, polyester, or any other material operable to apply compressive force to a wearer's foot and/or leg. In a preferred embodiment, the ankle support 615 is operable to provide graduated compression to the limb and foot of the user. In another embodiment, the ankle support 615 is multiple rings encircling the lower leg at various levels. These rings are additional layers of compression knit into the main body of the footwear object. This ankle support mechanism 615 replaces the need for several portions of tape that are often utilized to provide support to an athlete's ankle. In one embodiment, the ankle support mechanism is integral to the footwear object, providing toe, ankle, and general foot support in a single footwear object. The ankle support mechanism, in one embodiment, is non-adjustable. In another embodiment, the ankle support 615 is operable to be tightened or loosened by the user.

The footwear object as a whole is operable to extend, in one embodiment, from a toe to an area immediately below the knee. In another embodiment, the footwear object extends from a toe to an area below an ankle. In another embodiment, the footwear object extends from a toe to an area between the area below the ankle and the immediately below the knee.

Further illustrated in FIG. 6A are multiple zones of padding, including a heel pad 605 and toe pad 607. Operable to provide cushion and support around the heel and the toes as well as the ball of the foot, respectively, of the user, the heel pad 605 and toe pad 607 are constructed with one or more different materials, including, but not limited to, yarns and/or sheets made from nylon, polyester, spandex, silicone, neoprene, cotton, wool, merino wool, rayon, linen, silk, foams made from polyester, polyether, polystyrene, polyurethane, polyethylene or vinyl, rubbers, or metals such as copper. In one embodiment, the heel pad 605 and the toe pad 607 are constructed with materials of different composition and/or thickness. For example, in one embodiment, the heel pad 605 is made of multiple materials, such as cotton and spandex, and is 0.2 inches (5 mm) thick when uncompressed, and the toe pad 607 is made of additional materials, such as polyester, and is 0.1 inches (2.5 mm) thick when uncompressed. In a preferred embodiment, the heel pad 605 and toe pad 607 are formed of the same material as the body of the footwear object but with additional merino wool included in the knitted or woven pattern. In another embodiment, there are pads located at other positions throughout the footwear object to provide increased cushion, such as on the bottom of the footwear object in the arch region 303. Also illustrated in FIG. 6A are multiple grip zones, including a heel grip 601 and toe grip 603. The grip pads (601, 603) consist of a non-slip, gripping, friction-causing material on the underside of said footwear object and are placed around the heel as well as under the toes of the foot, respectively. The grip pads (601, 603) are woven into the footwear object, printed, thermally bonded, adhered, and/or otherwise applied to the footwear object. In a preferred embodiment, silicone is woven into the footwear object to form the heel grip 601 and toe grip 603. Silicone, or any other knittable material operable to improve grip and is knitted or woven in by way of various patterns, including but not limited to: rows, columns, a crossing pattern, circles, dots, or any other pattern operable to provide increased grip. In another embodiment, silicone is printed onto the footwear object to form the heel grip 601 and toe grip 603. Silicone, or any other printable material operable to approve grip, is applied by way of various patterns, including but not limited to: rows, columns, a crossing pattern, circles, dots, rectangles, triangles, abstract lines, or any other pattern operable to provide increased grip. In yet another embodiment, silicone or another grip enhancing material is both knitted or woven into the footwear object and printed onto the footwear object to form heel grip 601 and toe grip 603. In a non-limiting example, the one or more grip pads are areas of the footwear object that provide greater friction when compared to other areas of the footwear object. In another embodiment, the footwear object includes a grip zone covering the ball of the foot, located in the ball of foot region 309. In another embodiment, the footwear object includes grip zones located at other positions throughout the footwear object, such as along the arch of the foot in the arch grip zone 609, in order to provide increased traction for different user activities. In one embodiment, the arch grip zone includes silicone that is knit into the footwear object across the arch in order to provide increased grip. Silicone is operable to be knitted into, woven into, printed onto, or otherwise applied to the footwear object by way of various patterns, including but not limited to: rows, columns, a crossing pattern, circles, dots, or any other pattern operable to provide increased grip.

Also illustrated in FIG. 6A is a blister pad 613. The blister pad 613 covers the area below the ankle support 615 on the footwear object, comprising of the area from the top of the heel grip 601 to the bottom of the ankle support 61. The blister pad 613 is operable to cover the Achilles tendon area 623 of a user, or from below the Achilles tendon area 623 to slightly above the Achilles tendon area 623, along the back of the footwear object. The blister pad 613 is a densely knitted portion on the back of the ankle above the feel which is operable to minimize or prevent the formation of blisters for a user. In one embodiment, the blister pad 613 is formed of the same material as the body of the footwear object. In an alternative embodiment, one or more materials, such as, but not limited to, nylon, nylon 6, nylon 66, rayon, polyester, spandex, silicone, cotton, wool, merino wool, linen, silk, or still other types of natural and synthetic fibers, and fabrics that are blends and combinations of these fibers, are woven, knitted, sewn, or otherwise added to the footwear object in one or more additional layers to improve user comfort. In a preferred embodiment, the blister pad 613 is formed of the same material as the body of the footwear object but with additional merino wool included in the knitted or woven pattern.

Figure 6B:
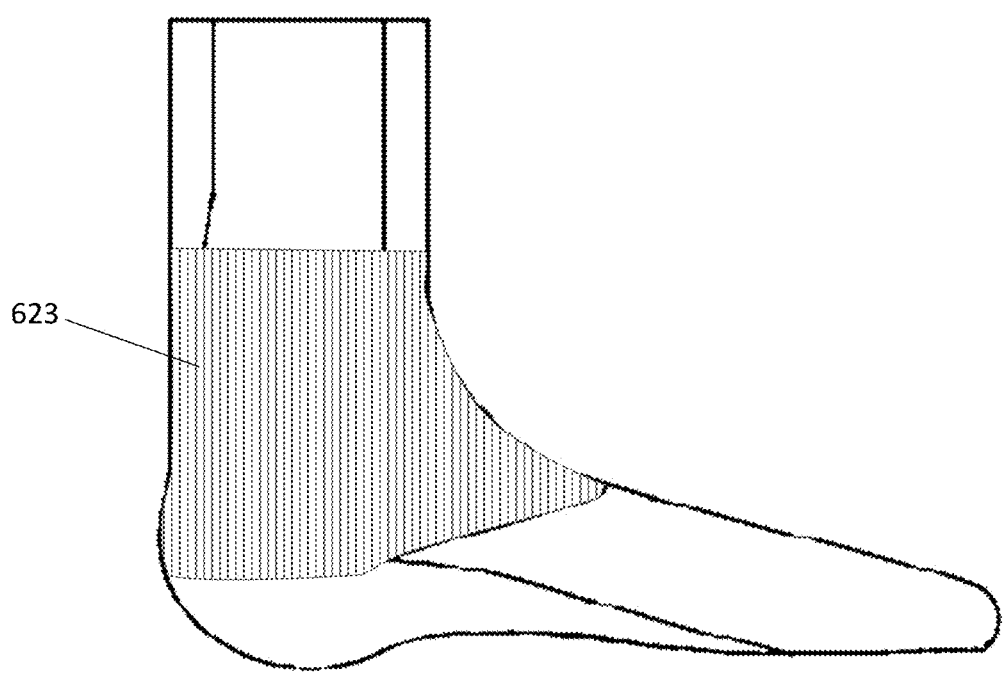
FIG. 6B illustrates a side view of a footwear object including an ankle support, according to one embodiment of the present invention.
Figure 6C:
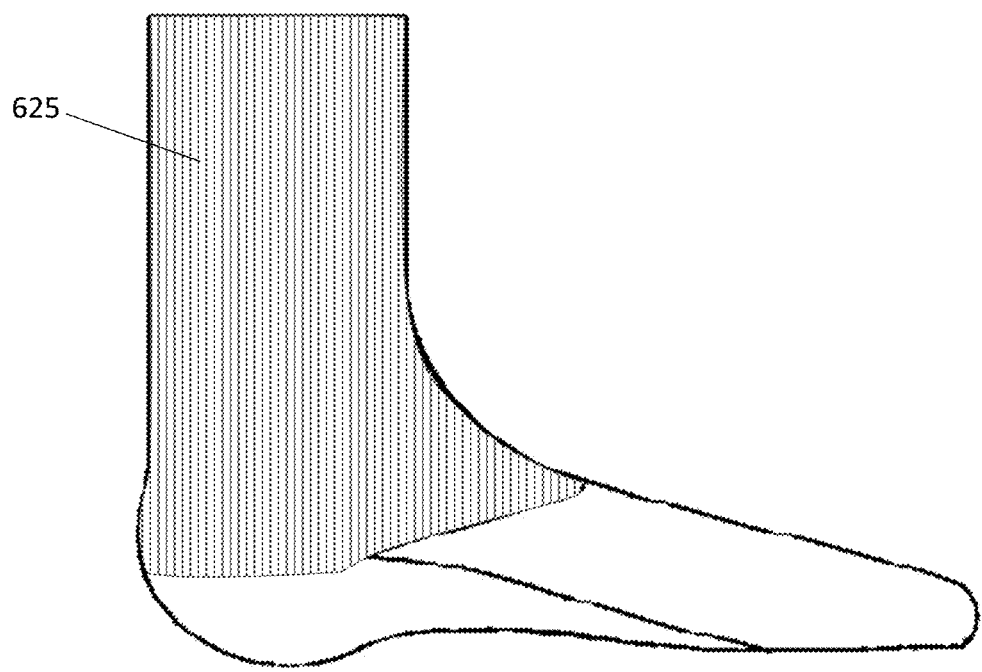
FIG. 6C illustrates a side view of a footwear object including an ankle support with a calf extension, according to one embodiment of the present invention.
Figure 6D:
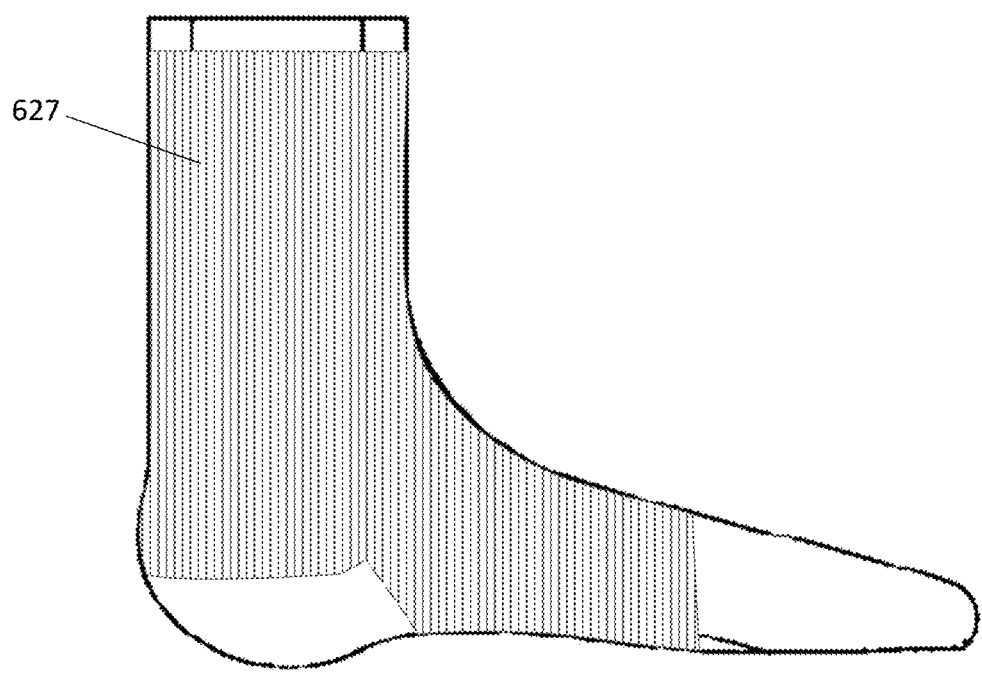
FIG. 6D illustrates a side view of a footwear object including an ankle support with a calf extension and arch extension, according to one embodiment of the present invention.
Figure 6E:
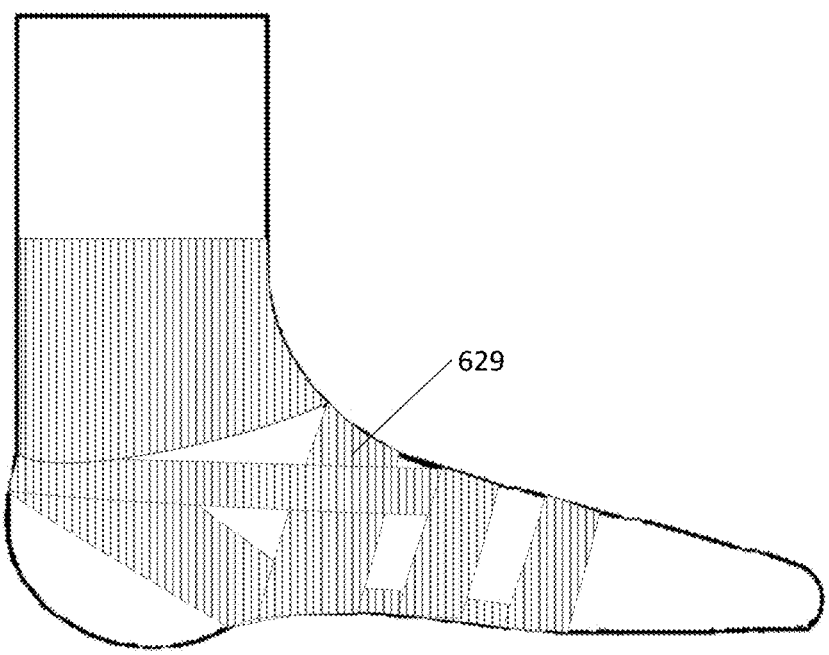
FIG. 6E illustrates a side view of a footwear object with a strapped ankle support according to one embodiment of the present invention.
Figure 6F:
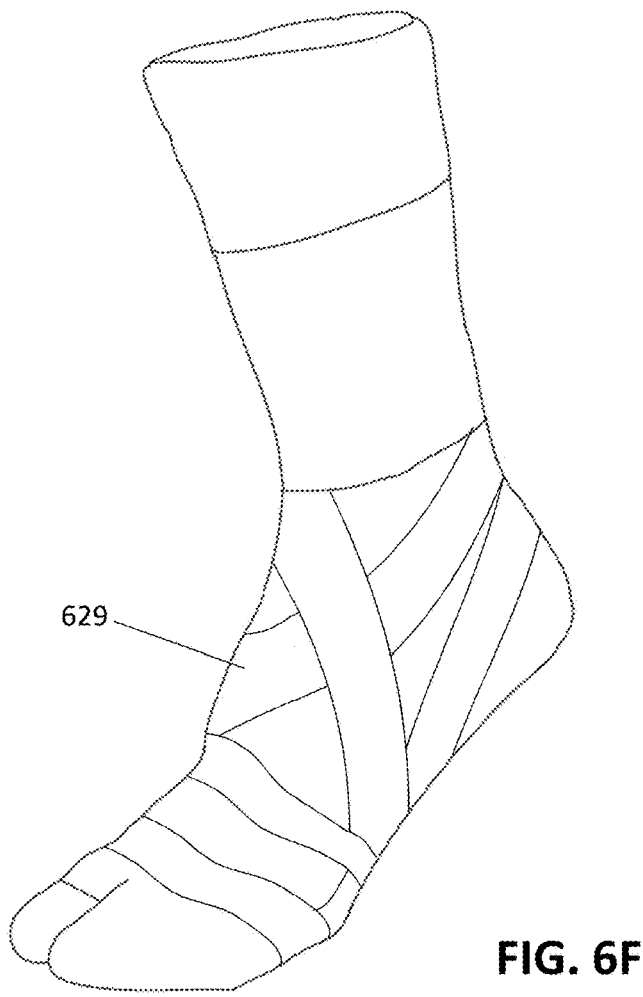
FIG. 6F illustrates a top perspective view of a footwear object with a strapped ankle support according to one embodiment of the present invention.

FIGS. 6B and 6C illustrate alternative embodiments of ankle support. FIG. 6B illustrates compressive low ankle support 623 which is operable to provide compression below the calf of a user and on the low ankle (making up the lower portion of calf region 307 and the upper portion of heel region 305). FIG. 6C illustrates a compressive full ankle support 625 which covers both the heel region 305 and the calf region 307 of the footwear object. Low ankle support 623 and full ankle support 625 are operable to be made in the same manner as ankle support 615. FIG. 6D illustrates a compressive full ankle support 625, wherein the full ankle support 625 extends toward an arch region. This advantageously provides compression benefits similar to a wrap or compression sleeve, wherein the compression area is constructed within the footwear object via a knitted or woven means or via non-woven construction methods that increase compression in the illustrated regions. FIG. 6E illustrates one embodiment of a strapped compression region, wherein the compression regions 629, wherein the strapped compression regions 629 are constructed within the footwear object via a knitted or woven means or via non-woven construction methods that increase compression in the illustrated regions. The strapped compression regions 629 provide targeted compression for specific areas of a foot, wherein readjustment of the footwear object provides for increased compression in one or more regions. In the illustrated embodiment, the strapped compression regions 629 cover an area below the ankle to approximately a ball of the foot. FIG. 6F illustrates a perspective view of another embodiment of strapped compression regions 629, wherein the strapped compression regions 629 cover an area below the ankle to approximately a ball of the foot.

Notably, any of the grip regions and/or compression regions are operable to be positioned with overlapping, integrated, embedded, or otherwise combined areas. For example, in one embodiment, a grip zone is positioned within a compressive region of the footwear object. In another embodiment, at least part of an arch compressive region overlaps with a grip zone and a toe strap and are woven into a single textile object.

Figure 7:
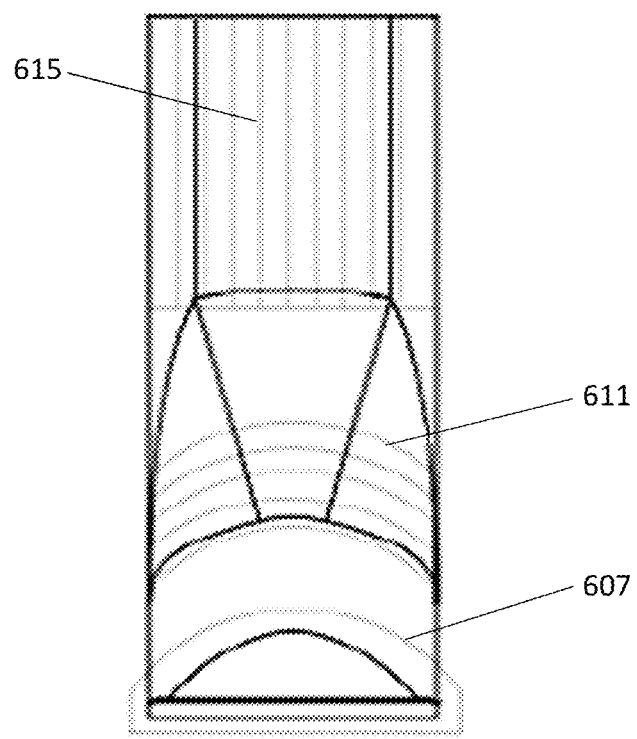
FIG. 7 illustrates a rear detail view of a footwear object having a woven and/or knitted material base, according to one embodiment of the present invention.

FIG. 7 provides a front view of one embodiment of a footwear object which includes multiple compression zones which are operable to create graduated compression. At the base of the figure is the toe pad 607, the compressive arch support 611, and the compressive ankle support 615.

Figure 8A:
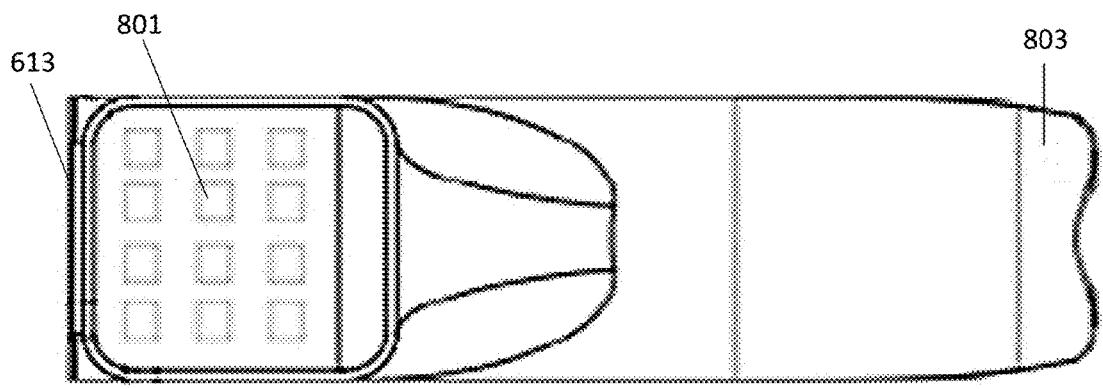
FIG. 8A illustrates a top detail view of a footwear object having a woven and/or knitted material base and a uniform toe box, according to one embodiment of the present invention.
Figure 8B:
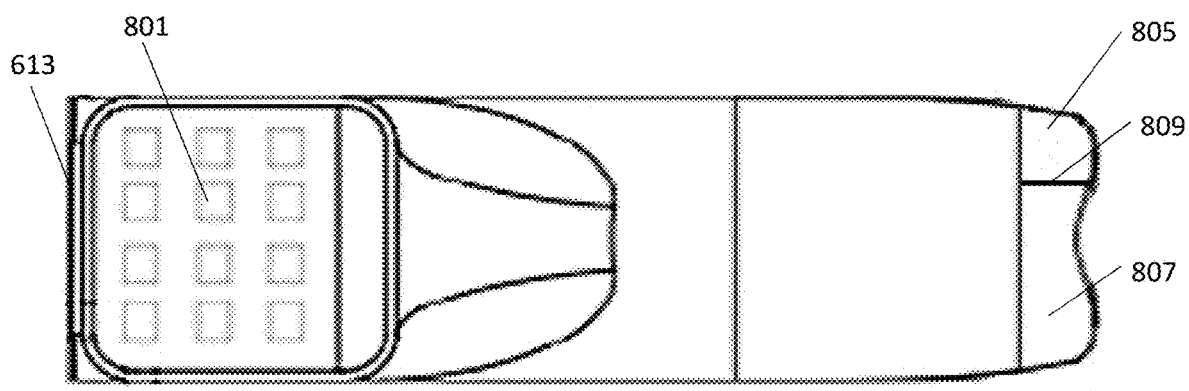
FIG. 8B illustrates a top detail view of a footwear object having a woven and/or knitted material base and a divided toe box, according to one embodiment of the present invention.
Figure 8C:
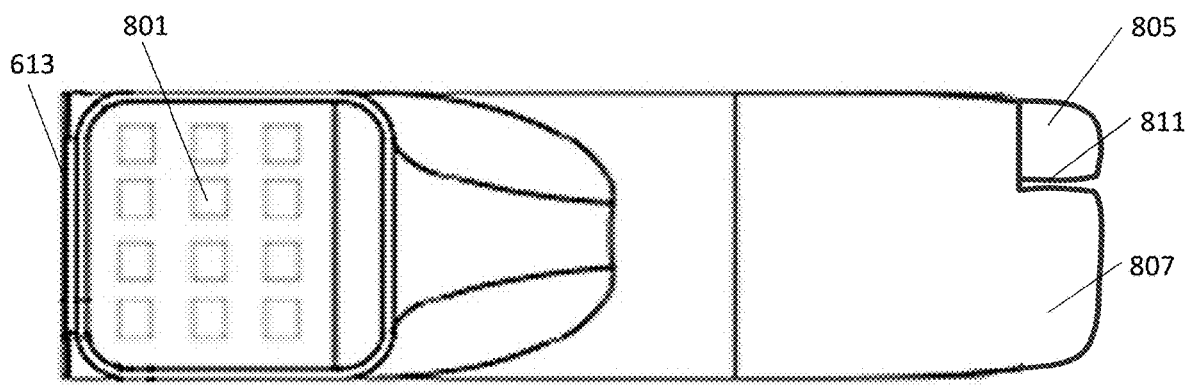
FIG. 8C illustrates a top detail view of a footwear object having a woven and/or knitted material base and a split toe box, according to one embodiment of the present invention.

FIGS. 8A, 8B, and 8C illustrate alternative embodiments of a footwear object that includes internal grip zones 801. The internal grip zones 801 are placed on the inside of the footwear object, and are operable to make contact with the skin of the foot of the user in order to prevent the foot of the user from moving within the footwear object. In one embodiment, the internal grip zones 801 are made of silicone or a silicone blend and are printed onto the footwear object. In an alternative embodiment, the internal grip zones 801 are made of any other material operable to increase the coefficient of friction between the foot of the user and the footwear object, such as, but not limited to, rubber, polyurethane, silicone, and bamboo fibers. Alternatively, the internal grip zones 801 are applied by any other chemical or adhesive bonding. In one embodiment, the internal grip zones 801 are an array of small rectangles. In another embodiment, the internal grip zones 801 are an array of small circles, sets of lines, concentric circles, or any other pattern operable to provide increased grip. In each of FIGS. 8A, 8B, and 8C, a blister pad 613 is also shown.

FIGS. 8A, 8B, and 8C each demonstrate a different means of toe containment. FIG. 8A illustrates a top detail view of one embodiment wherein all of the toes are in one uniform toe box 803 and are not separated. FIG. 8B illustrates a top detail view of one embodiment wherein there is a divided toe box comprised of a medial toe compartment 805 and a lateral toe compartment 807, which are divided by a closed toe partition 809 inside of the sock. In yet another example, the closed toe partition 809 is formed by joining the top of the sock with the bottom of the sock, creating a partition that separates two or more given toes. FIG. 8C illustrates a top detail view of one embodiment wherein there is a divided toe box comprised of a medial toe compartment 805 and a lateral toe compartment 807, which are divided by a separated toe partition 811. The separated toe partition 811 creates a gap between the medial toe compartment 805 and a lateral toe compartment 807, allowing them to move independently.

FIGS. 9A, 9B, 9C, 9D, 9E, and 9F illustrate alternative embodiments of a footwear object that each include multiple grip zones, a toe strap, and different means of toe containment. Each figured illustrates a heel grip 601. The heel grip 601 consists of a non-slip, gripping, friction causing material on the underside of said footwear object which wraps around the heel. In a non-limiting example, the heel grip 601 is an area of the footwear object that provide greater friction when compared to other areas of the footwear object. In another embodiment, the heel grip 601 is comprised of two or more zones that are equal in size. In another embodiment, the heel grip 601 is comprised of two or more zones that are unequal in size. In an alternative embodiment, the heel grip 601 is an array of small rectangles. In another embodiment, the heel grip 601 is an array of small circles, sets of lines, concentric circles, or any other pattern operable to provide increased grip. FIGS. 9A, 9B, 9C, 9D, and 9F also illustrate the bottom side of a toe strap 901. In one embodiment, the toe strap 901 originates from in front of the heel grip 601 on the underside of the food, crosses over the underside of the foot, extends over the front of the hallux, and terminates on top of the hallux, and the hallux is isolated from the rest of the toes. In another embodiment, the toe strap 901 extends from the very back of the heel or from anywhere within the heel region 305. In yet another embodiment, the toe strap extends from a position within the arch region 303 or from a position within the toe region 301. In yet another embodiment, the toe strap extends from the medial side of the footwear unit, from the middle of the footwear unit, from the lateral side of the footwear unit, or a location in between the medial side and middle or lateral side and middle. The toe strap 901 is formed in such a manner that it is not as elastic as the remainder of the footwear object. For example, elongation in one embodiment of the footwear object was measured through a test, wherein a point on the footwear object on top of a point on a user's toe was marked while worn by a user, the footwear object was bent approximately 90-degrees by the user's toe, and displacement of the point on the user's toe from the point on the footwear object was recorded. In one embodiment, elongation for a sock sized for and worn by a user with men's shoe size 7.5-10.5 (approximately is between 9.375 inches and 10.375 inches (23.8 centimeters and 26.2 centimeters)) is approximately 0.3 centimeters and 0.7 centimeters (0.118 inches and 0.276 inches). In another embodiment, elongation is between 0.3 centimeters and 0.6 centimeters (0.157 inches and 0.236 inches). In a preferred embodiment, elongation is less than or equal to 0.4 centimeters (0.157 inches).

In one embodiment, the toe strap 901 is formed of at least one layer of nylon. In another embodiment, the toe strap 901 is formed of artificial fibers such as, but not limited to, nylon 6, nylon 66, rayon, polyester, spandex, silicone, and others, or natural fibers such as cotton, wool, merino wool, linen, silk, or still other types of natural and synthetic fibers, and fabrics that are blends and combinations of these fibers. In one embodiment, toe strap 901 comprises 560 denier spandex yarn and polyester yarn and is operable to resist the elongation of the footwear object, wherein the polyester yarn is SORBTEK. Toe strap 901 is attached to the footwear object by chemical, physical, or adhesive bonding, or is knitted, woven, or sewn into the footwear object. In this configuration, the toe strap is adapted to prevent hyperextension of the hallux by limiting the range of motion of the hallux. In a preferred embodiment, the toe strap limits the range of motion due to its being woven, due to the choice of fibers woven into the toe strap, or a combination these structural elements. In another embodiment, the toe strap is knitted. Toe strap 901 is operable to be made in different widths for different sized footwear units. In one embodiment, the toe strap 901 is between 0.01 and 2 mm thick, and between 1 mm and 40 mm wide. In another embodiment, the toe strap 901 is between 0.03 and 1.3 mm thick, and between 5 mm and 30 mm wide. In one embodiment, the toe strap 901 applies tension to at least one compartment of the footwear object.

In one embodiment, a toe grip 603 runs laterally to the toe strap 901, under the ball of the foot, and under the toes. In a non-limiting example, the toe grip 603 is an area of the footwear object that provide greater friction when compared to other areas of the footwear object. In another embodiment, the toe grip 603 is comprised of two or more zones that are equal in size. In another embodiment, the toe grip 603 is comprised of two or more zones that are unequal in size. In an alternative embodiment, the toe grip 603 is an array of small rectangles. In another embodiment, the toe grip 603 are an array of small circles, sets of lines, concentric circles, or any other pattern operable to provide increased grip. In yet another embodiment, toe grip 603 also runs medially to the toe strap 603 in order to cover a larger area on the underside of the footwear object. FIG. 9F illustrates an alternative embodiment of grip enhancement, arch grips 913. Arch grips 913 are located medially to the toe strap 901 within the arch region 303. Arch grips 913 are operable to be applied to the footwear object in any of the same methods as toe grip 603.

Figure 9A:
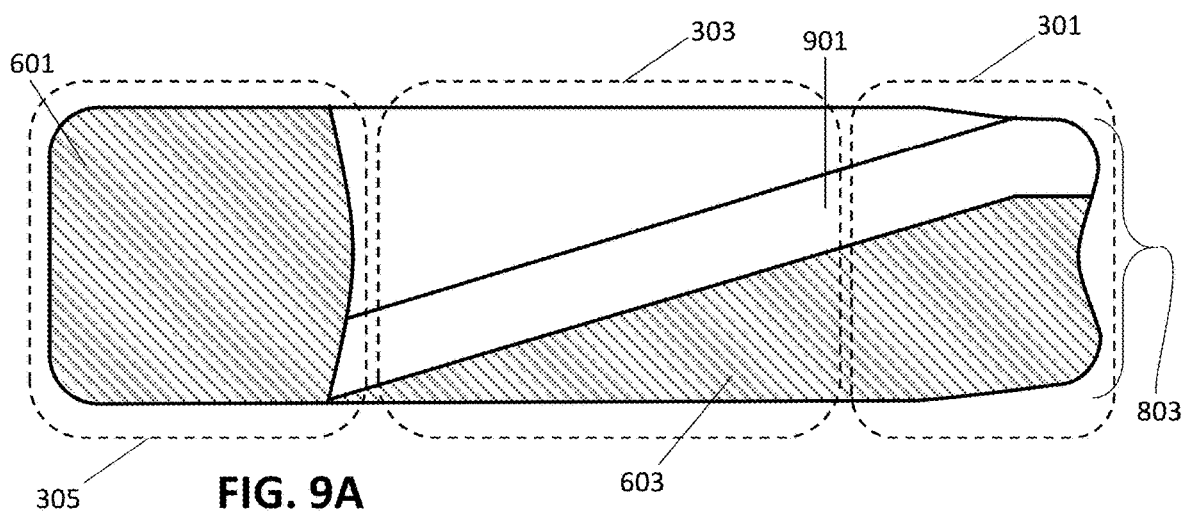
FIG. 9A illustrates a bottom detail view of a footwear object with a uniform toe box, according to one embodiment of the present invention.
Figure 9B:
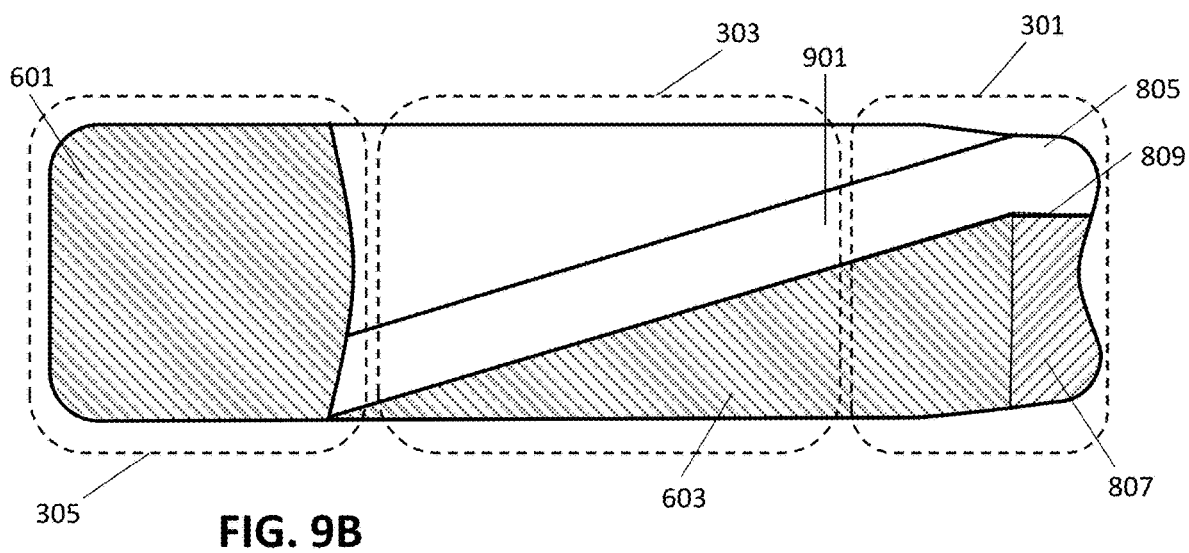
FIG. 9B illustrates a bottom detail view of a footwear object with a divided toe box, according to one embodiment of the present invention.
Figure 9C:
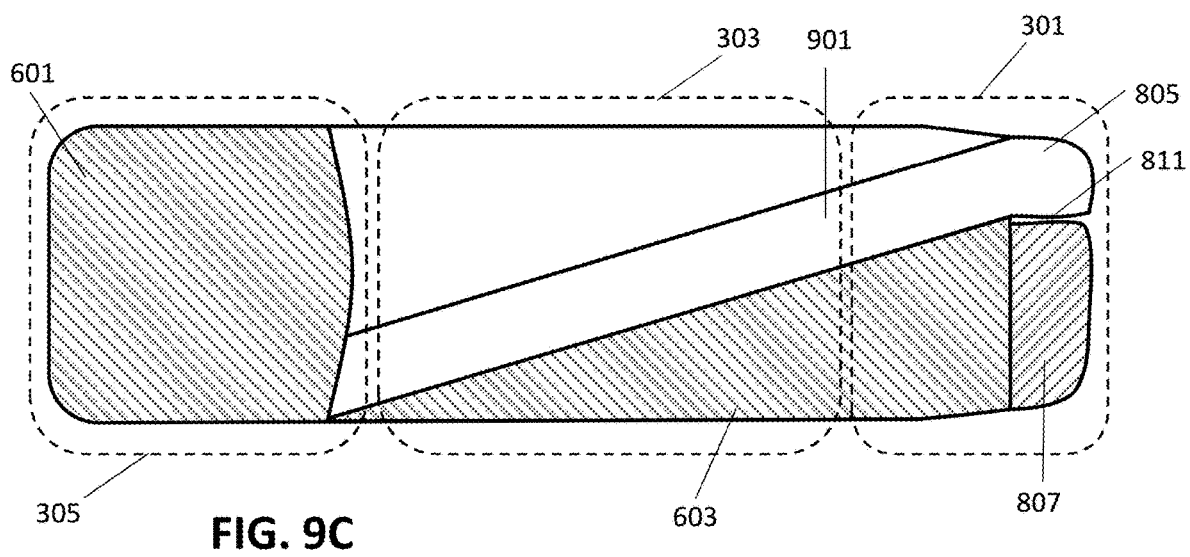
FIG. 9C illustrates a bottom detail view of a footwear object with a split toe box, according to one embodiment of the present invention.
Figure 9D:
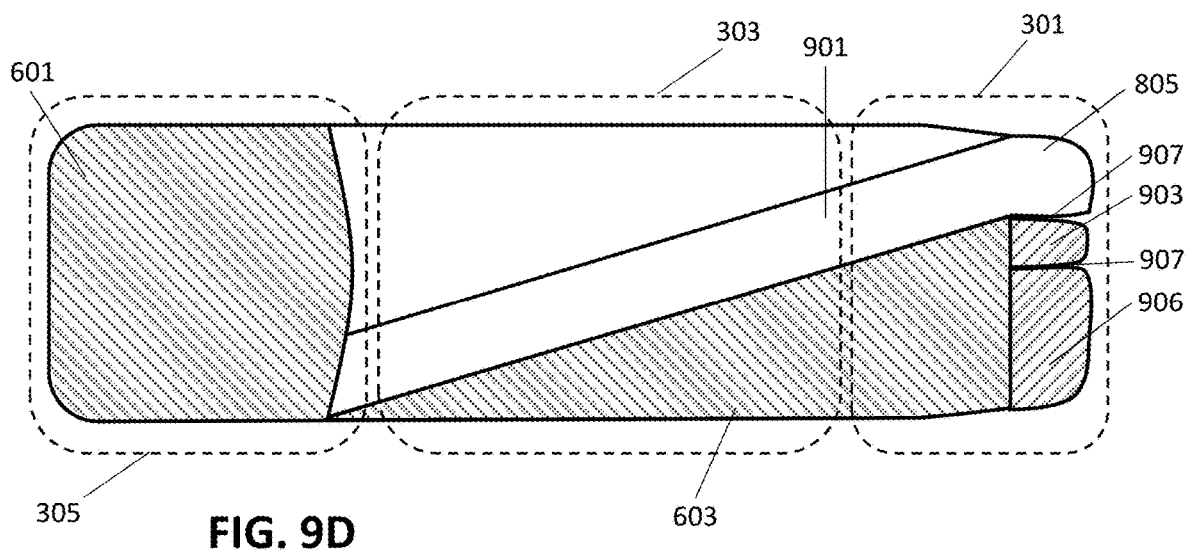
FIG. 9D illustrates a bottom detail view of a footwear object with multiple split toe boxes, according to one embodiment of the present invention.
Figure 9E:
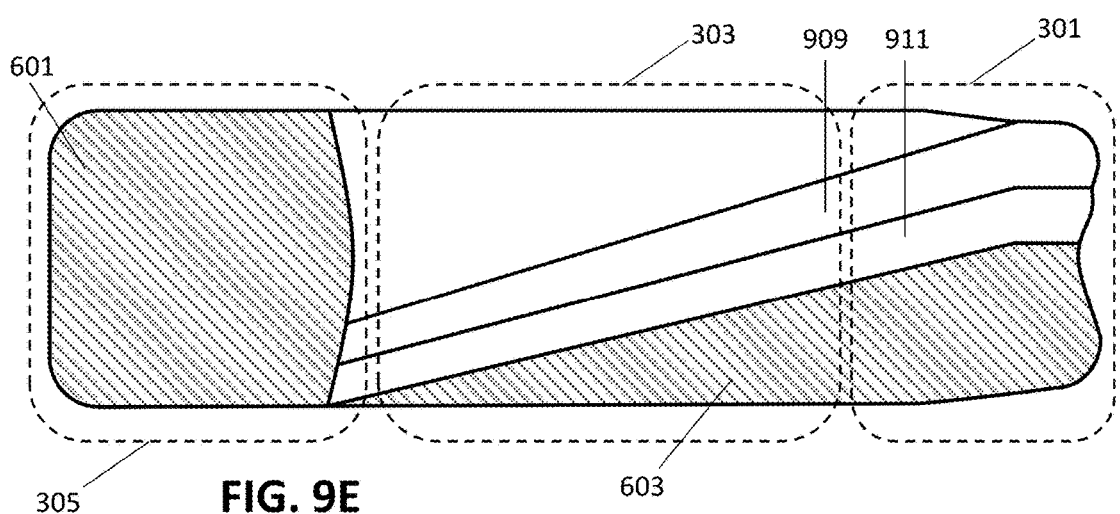
FIG. 9E illustrates a bottom detail of a footwear object with multiple toe straps, according to one embodiment of the present invention.
Figure 9F:
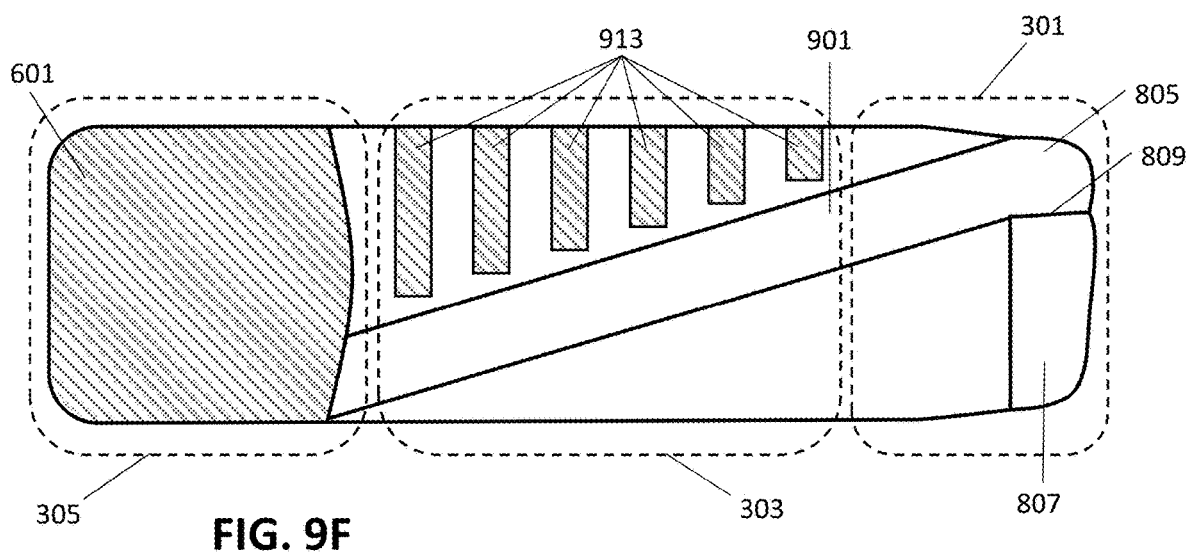
FIG. 9F illustrates a bottom detail view of a footwear object with a medial grip zone, according to one embodiment of the present invention.

FIGS. 9A, 9B, 9C, 9D and 9E each demonstrate a different means of toe containment. FIG. 9A illustrates a bottom detail view of one embodiment wherein all of the toes are in one uniform toe box 803 and are not separated, meaning all of the tows of a foot are covered by the footwear object. The toe strap 901 continues around the toe box 803 from the bottom side to the top side, as does the toe grip 603. FIG. 9B illustrates a bottom detail view of one embodiment of a divided toe box comprising a medial toe compartment 805 and a lateral toe compartment 807, wherein the medial toe compartment 805 and the lateral toe compartment 807 are divided by a closed toe partition 809 inside of the sock. In one embodiment, the toe strap 901 continues around the medial toe compartment 805 from the bottom side to the top side, and the toe grip 603 continues around the lateral toe compartment 807 from the bottom side to the top side. In yet another example, the closed toe partition 809 is formed by joining the top of the sock with the bottom of the sock, creating a partition that separates two or more given toes. In another embodiment, the closed toe partition 809 is formed from a piece of plastic, metal, knitted or woven fabric or other material fixedly attached into the footwear object to create a partition that separates two or more given toes. FIG. 9C illustrates a bottom detail view of one embodiment wherein there is a divided toe box comprised of a medial toe compartment 805 and a lateral toe compartment 807, which are divided by a separated toe partition 811. The separated toe partition 811 creates a gap between the medial toe compartment 805 and a lateral toe compartment 807, allowing them to move independently. In one embodiment, the toe strap 901 continues around the medial toe compartment 805, and the toe grip 603 continues around the lateral toe compartment 807. In an alternative embodiment, there are holes in the end of the footwear object, allowing toes to be outside of the footwear object. In another embodiment, there are three or more toe compartments. FIG. 9D illustrates another embodiment where there are three or more toe compartments, a medial toe compartment 805, small lateral toe compartment 906, and middle toe compartment 903. These three toe compartments are divided by separated toe partitions 907. FIG. 9E illustrates an alternative embodiment of the present invention, where there are two toe straps, first two strap 909 and second toe strap 911. These toe straps (909, 911) serve the same principle as toe strap 901, but multiple are present, and each of the first toe strap 909 and second toe strap 911 act on an individual toe compartment. In one embodiment, first toe strap 909 acts on a first toe compartment for the hallux, and second toe strap 911 acts on a second toe compartment for the long toe, also known as the second toe.

In a preferred embodiment, the toe supporting mechanism made up of the toe strap 901 and toe compartments (805, 807) provides for support of the toe ligaments, prevents the full weight of the foot from concentrating on the toes, and provides for proper positioning of the toes to maintain function and prevent injury. In an alternative embodiment, the toe support mechanism is a separate attachment that is connected to the footwear object and provides the same or very similar functions as the toe support mechanism that is an integral portion of the construction of the footwear object. Additionally, the toe strap limits the range of motion due to the woven pattern of the toe strap, due to the choice of fibers woven into the toe strap, or a combination these structural elements. In yet another embodiment, the toe strap starts on the bottom of the footwear object at a position in front of the heel and runs towards the front of the footwear object, passing across an arch and from one side to the other, curving up and over the front of the foot, and ending at a position on top of multiple toes, or multiple toes and the hallux, limiting the range of motion of that those toes and/or hallux. In one embodiment, the toe strap 615 is permanently fixed to the footwear object and is not adjustable. In an alternative embodiment, the toe strap 615 is operable to be adjusted by the user in order to provide more or less tension as needed.

FIG. 9G illustrates a table identifying angles of impending motion for various embodiments of the present invention. The test was conducted by placing a 3 pound (1.36 kilogram) weight on a 6×2 inch (15.24×5.08 centimeter) footwear object sample including bottom grip elements. Various silicone varieties for grip were used, and footwear objects with both knit and printed silicone were tested. The sample was attached to the weight, and a layer of 100% spunbond polyester was placed below the sample. The spunbond polyester was attached to a glass platform of a testing apparatus. The platform of the testing apparatus was raised, and an angle at which the weight overcame static friction was identified. These angles of impending motion were recorded and averaged. Samples were then wetted and retested. Averaged results of these tests are reproduced in FIG. 9G.

Figure 10:
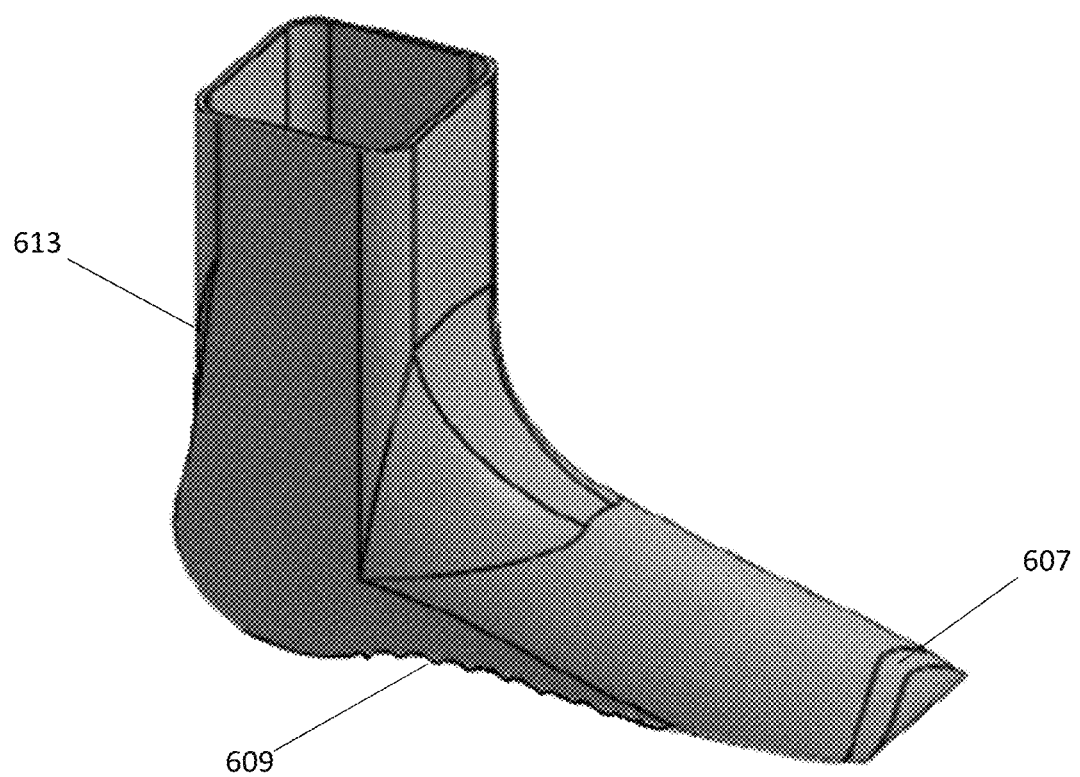
FIG. 10 illustrates an isometric view of a footwear object having a woven and/or knitted material base, according to one embodiment of the present invention.

FIG. 10 illustrates an isometric view of a footwear object having a woven and/or knitted material base, according to one embodiment of the present invention. From this perspective, multiple components of the invention are visible. On the back of the footwear object is the blister pad 613. On the bottom of the footwear object is the arch grip zone 609. At the front of the footwear object is the toe pad 607.

Figure 11A:
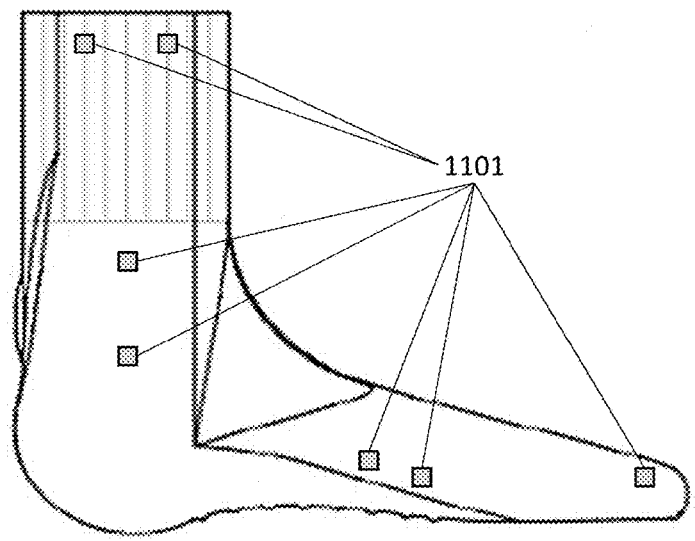
FIG. 11A illustrates a side detail view of a footwear object with sensors, according to one embodiment of the present invention.
Figure 11B:
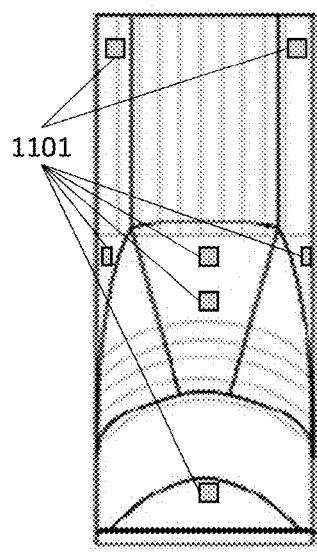
FIG. 11B illustrates a front detail view of a footwear object with sensors, according to one embodiment of the present invention.
Figure 11C:
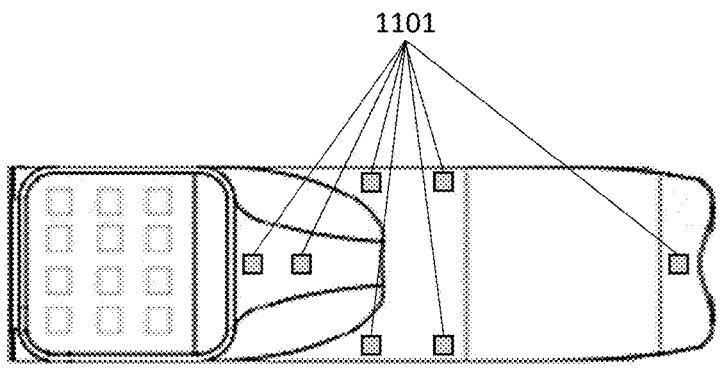
FIG. 11C illustrates a top detail view of a footwear object with sensors, according to one embodiment of the present invention.

FIGS. 11A, 11B, and 11C illustrate another embodiment of the footwear object injury prevention device, wherein the footwear object includes sensing and communications capabilities. FIGS. 11A, 11B, and 11C illustrate side, front, and top views, respectively of a footwear object with one or more microchips 1101. In one embodiment, the one or more microchips 1101 include a control unit, wherein the control unit is in direct network communication with one or more sensors or is wirelessly connected to one or more sensors. The microchips 1101 are operable to communicate via any wired or wireless communication means, including via IEEE 802.11 wireless communication protocols, including BLUETOOTH, NEAR FIELD COMMUNICATION (NFC), and WIFI. The microchips 1101 are further operable to interface with one or more external devices, including strain gauges, accelerometers, Electromagnetic Field generators, and/or other sensors or computing devices. In another embodiment, at least one of the microchips 1101 includes a battery. Sensors are operable to be constructed with any size, shape, or materials that effectively perform sensing and communication operations within the footwear object. In one embodiment, sensors include conductivity, resistance, capacitance, ultrasound, optical, microwave, and/or any other electrical, chemical, or mechanical sensing functionality. Variables detectable by the sensors include, in one embodiment, fluid presence, fluid volume, fluid distribution, temperature, pressure, stress-strain, movement, acceleration, impact, velocity, humidity, location, and conductivity-resistance, as well each of any additional variables and metrics necessary for measurement of athletic performance or injury identifiers. Devices integrated within products are operable to be constructed with coverings, encasings, laminations, or other protective coatings for durability and reuse. In one embodiment, the sensors are biodegradable, biocompostable, recyclable, and/or eco-friendly. Sensors preferably include one or more sensing capabilities within a single microchip or a network of microchips, wherein the sensors are operable to detect a single variable, a combination of variables, and/or wherein individual sensors in a network of sensors are operable to communicate a variety of variables to a single controller or computing device. The sensors are operable to collect the variety of variables as usage metrics and communicate the collected usage metrics to a single controller, computing device, or communication network. In a further embodiment, the system includes one or more sensor networks, wherein a collection of sensors or sensing elements are in network communication with one or more computing devices and/or control units. Sensors either each include individual control units or are each connected to a single control unit. Notably, sensors are operable to detect any variables associated with a footwear object, its user, or an external environment. For example, in one embodiment, one or more temperature sensors are operable to detect a temperature external to an object, a temperature on, between, or within one or more layers, and/or a temperature of a user's skin or body. Sensors are further operable to detect any other variable directly or indirectly associated with the footwear object, its environment, and its user. For example, in one embodiment, one or more sensors are operable to detect, individually or in combination, a pulse of a user, a volume of moisture (such as sweat) absorbed, and an external temperature.

In one embodiment, sensors include at least a control unit, a sensing apparatus, and a power source, wherein the sensor is preferably portable and wireless. The control unit, in one embodiment, includes a wireless antenna for communication to one or more external devices. The wireless antenna is, in one embodiment, BLUETOOTH (including BLUETOOTH LOW ENERGY), WI-FI (including all IEEE 801.11 communication methods at 2.5 GHz, 5 GHz, 60 GHz, or otherwise), cellular (e.g., 5G, Long Term Evolution (LTE), Code-Division Multiple Access (CDMA), Enhanced Data GSM Environment (EDGE), Evolution-Data Optimized (EVDO), an/or any other digital or analog methods of communication. In one embodiment, a power source operated by a single-use battery. In another embodiment, the battery is rechargeable (e.g., a lithium-ion battery or any chemical or solid-state reusable power sources). One or more batteries are connected to one or more control units for each sensor. Sensors are operable to be in connection with the control unit directly and/or are operable to be in network communication with the control units via wired or wireless means.

In a further embodiment, the footwear object includes at least one geopositioning sensor or device and generates, tracks, and stores corresponding location data. Location data is generated using one or more hardware and/or software components. By way of example and not limitation, location data is created using satellite-based positioning systems (e.g., Global Positioning System (GPS), Differential GPS (DGPS), or Galileo), low energy BLUETOOTH including BLUETOOTH LOW ENERGY (BLE) based systems such as beacons, wireless networks such as WI-FI, Radio Frequency (RF) including RF Identification (RFID), NEAR FIELD COMMUNICATION (NFC), magnetic positioning, cellular triangulation, and/or combinations of these technologies. By way of example, location data is determined via an Internet Protocol (IP) address of a device connected to a wireless network. A wireless router is also operable to determine identities of devices connected to the wireless network through the router, and thus is operable to determine the locations of these devices through their presence in the connection range of the wireless router. Location data is communicated, stored, tracked, and analyzed on at least one device integral with the footwear object, at least one device external to the object, a computing device in communication with one or more elements of the article, and/or one or more external servers, computers, databases, and/or cloud networks. In another embodiment, the location data is associated with one or more sensors, one or more footwear objects, and/or one or more users. For example, in one embodiment, the system is operable to provide geographical, activity, and/or personal health tracking information for a footwear object worn by a player running around a field.

FIG. 11A illustrates one embodiment of sensor locations within a footwear object, wherein the sensors are positioned along a calf of the footwear object, along an ankle of the footwear object, on an arch of the footwear object, and/or on at least one compartment of a toe region of the footwear object. The sensors are operable to be positioned on an inside of the footwear object for direct contact with skin of a user, between one or more layers, or on an outside of the footwear object. FIGS. 11B and 11C illustrate a front view and a top view of the footwear object illustrated in FIG. 11A.

Figure 12A:
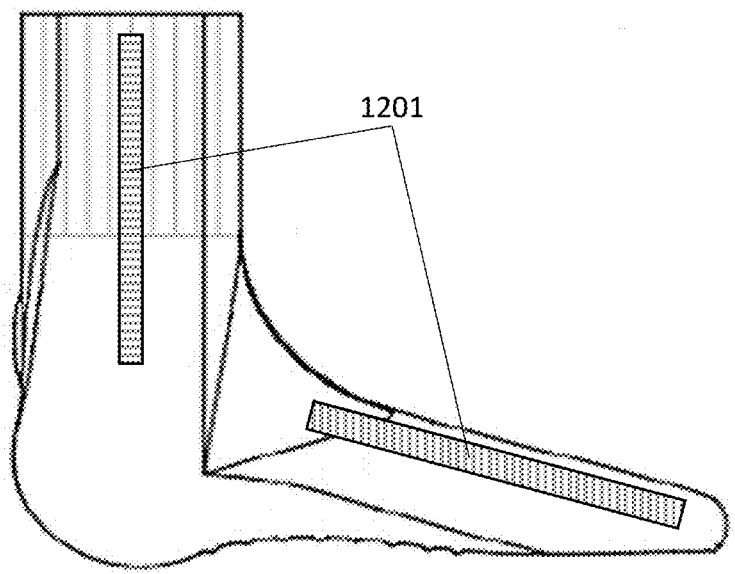
FIG. 12A illustrates a side detail view of a footwear object with sensors, according to one embodiment of the present invention.
Figure 12B:
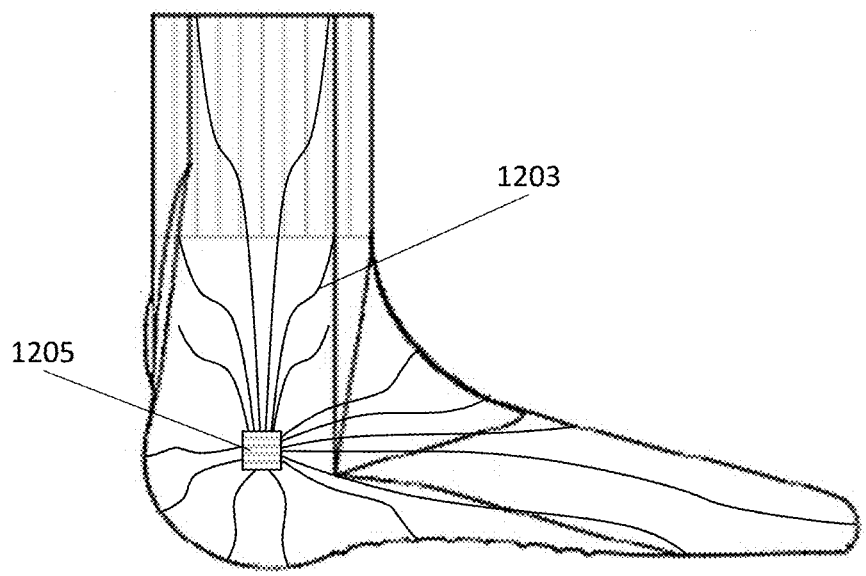
FIG. 12B illustrates a side detail view of a footwear object with sensors, according to one embodiment of the present invention.

FIG. 12A illustrates an alternative embodiment of sensor locations, wherein one or more strips of sensors 1201 are used to obtain and collect data during use of the footwear object. Examples of this data include collection of sweat by the footwear object or stress-strain experienced by the top of the foot. The sensors 1201 are operable to be positioned on an inside of the footwear object for direct contact with skin of a user, between one or more layers, or on an outside of the footwear object. In one embodiment, the sensors 1201 are located across the toe region 301, vertically oriented along the calf region 307, on top of or under the toe strap 901, interwoven with the grip elements (601, 603), or in any other region that can provide relevant information. FIG. 12B illustrates an alternative embodiment of sensor locations on a footwear object, wherein the sensing elements 1203 extend along the vertical and horizontal lengths of the footwear object and are woven or knitted into the footwear object. In one embodiment, the sensing elements 1203 are connected to a control unit 1205 directly. In another embodiment, the sensing elements 1203 are connected wirelessly to a control unit 1205.

Figure 13A:
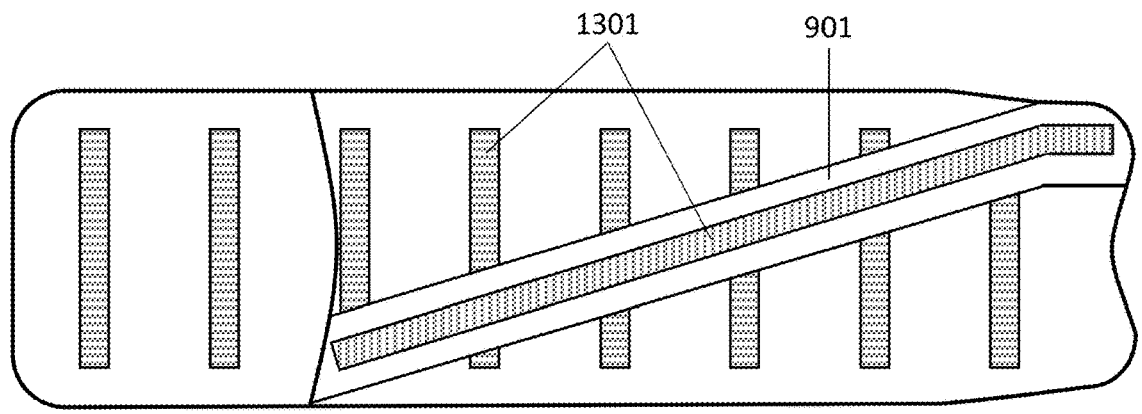
FIG. 13A illustrates a bottom detail view of a footwear object with sensors, according to one embodiment of the present invention.
Figure 13B:
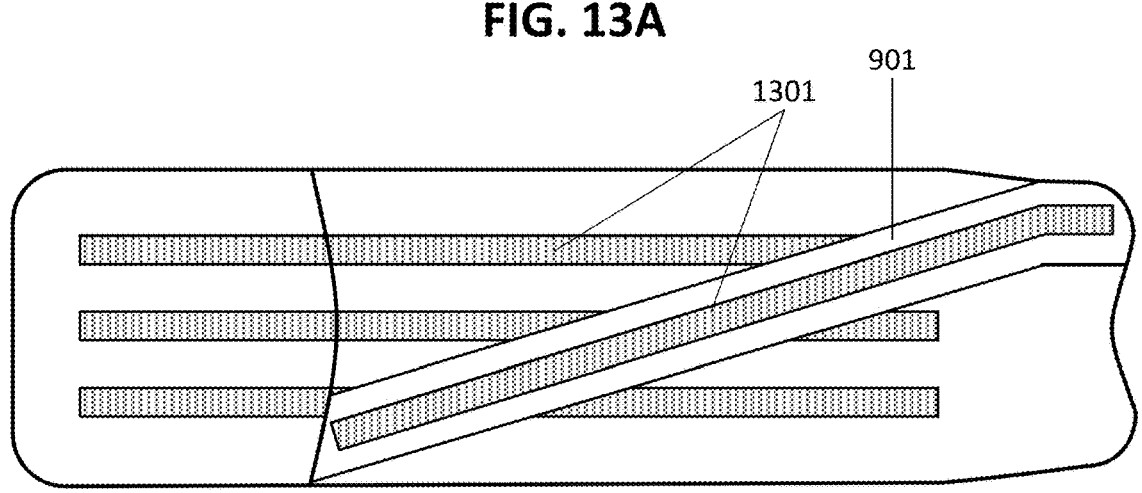
FIG. 13B illustrates a bottom detail view of a footwear object with sensors, according to one embodiment of the present invention.
Figure 13C:
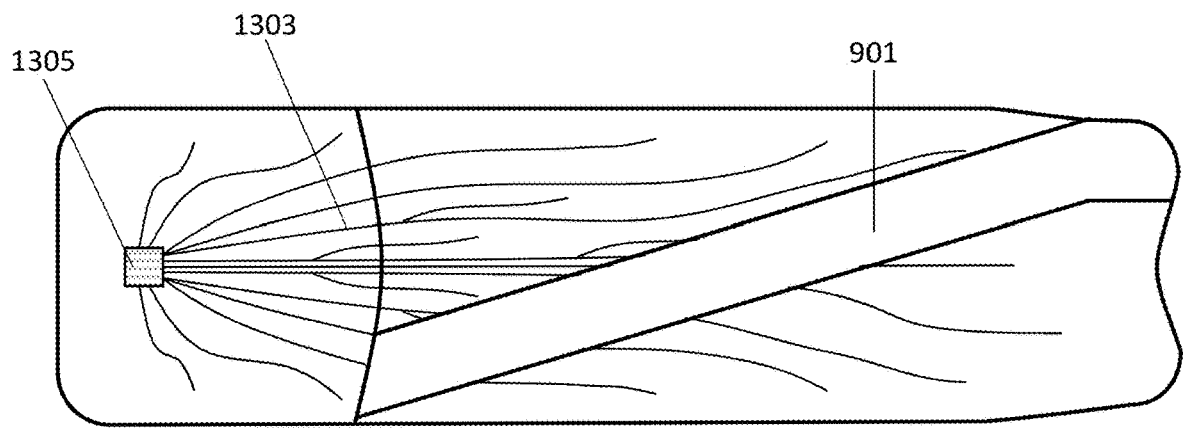
FIG. 13C illustrates a bottom detail view of a footwear object with sensors, according to one embodiment of the present invention.

FIGS. 13A, 13B, and 13C illustrate alternative embodiments of sensor locations located on the bottom of the footwear object. These sensors measure one or more environmental or user variables, including pressure exerted by different locations of the foot and the stress-strain experienced by the foot, including the strain experienced during hyperextension of the hallux. FIGS. 13A and 13B illustrate multiple strip sensors 1301, including a strip sensor 1301 that is placed along the length of the toe strap 901. FIG. 13C illustrates an alternative embodiment of sensor locations on a footwear object, wherein the sensing elements 1303 extend along the length of the footwear object. In one embodiment, the sensing elements 1303 are connected to a control unit 1305 directly. In another embodiment, the sensing elements 1303 are connected wirelessly to a control unit 1305.

In one embodiment, the sensor is operable to communicate with one or more external devices and systems. For example, in one embodiment, the sensor is in network communication with one or more mobile phone applications, mobile phones, desktops, desktop applications, dedicated sensor computer systems, servers, cloud networks, alarms, and/or any other external computer devices. The sensor is operable to provide real time, near-real time, periodic, or on-demand updates to the one or more external computer devices, wherein the updates include raw data from the sensor, processed data from the sensor, or alerts when certain environmental conditions have been met. For example, in one embodiment, a calibrated sensor determines that the footwear object is traveling at a specific speed. Based on the sensed value, the sensor is operable to send a push notification to an application on at least one mobile phone, wherein the push notification includes an alert about the athlete's performance. In another embodiment, the sensor is in network communication with a mobile application, which receives and processes the sensor data directly on the mobile device.

In one embodiment, an application for a computing device (e.g., a mobile phone, personal computer, server, or cloud network) is operable to receive, store, process, analyze, and make recommendations based on raw or processed sensor data. For example, in one embodiment, a mobile application is operable to sync event data to at least one server and at least one cloud network, wherein event data includes raw sensor data, measured velocities and accelerations, determined athlete pulse, an attained maximum stress-strain, and/or other sensed conditions. A remote server computer, a cloud network, and/or a mobile application is operable to further receive and sync secondary health data via a mobile application, through "smart" devices (e.g., digital scales, toothbrushes, toilets, refrigerators, fitness trackers, smart watches, other devices with networking, communication, logging, and tracking capabilities). In one embodiment, the remote server computer, the cloud network, and/or the mobile application is further operable to generate graphs, charts, tables, and other trend visualizations for the sensed variables.

The system additionally includes, in one embodiment, at least one database, wherein the database is directly or remotely connected to a sensor or microchip of the footwear object, a computing device in direct communication with the sensor or microchip, a remote computer device, a server, and/or a cloud network. The system is operable to create and store unique user accounts for the data collected, analyzed, or generated by the system. The system is operable to provide access to the data through a mobile application, through a browser, or through any other means of receiving communicating data via a network (e.g. a local network or the Internet). In one embodiment, user accounts and user account data are protected by a number of security constraints, including password protection, encryption, abstraction, or other security protocols. In an alternative embodiment, multiple user accounts are connected to an administrator account, allowing one or more individuals to track the data collected for multiple individuals, such as for a team.

Figure 14:
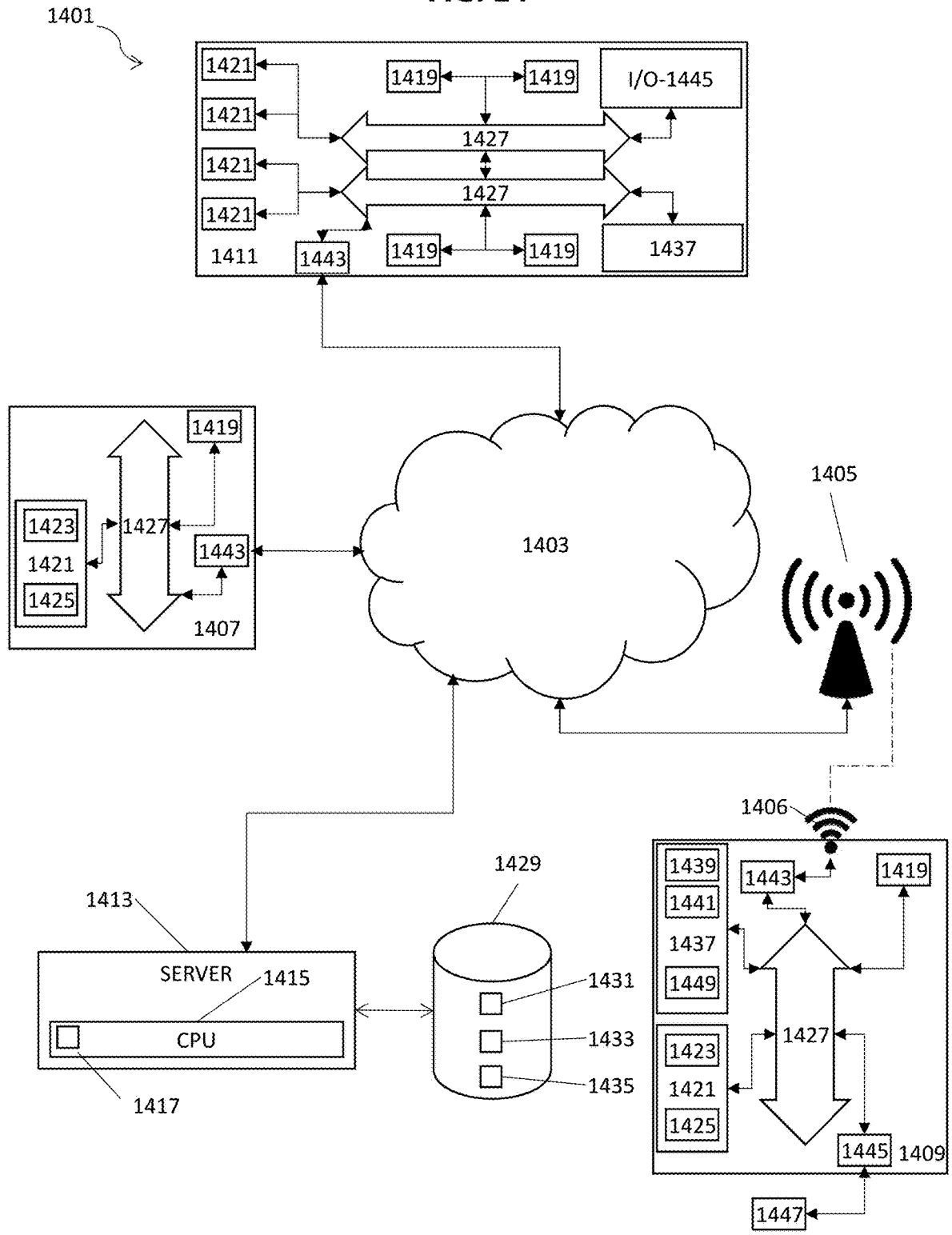
FIG. 14 is a schematic diagram of a system of the present invention.

FIG. 14 is a schematic diagram of an embodiment of the invention illustrating a computer system, generally described as 1401, having a network 1403, a plurality of computing devices 1407, 1409, 1411, a server 1413, and a database 1429.

The server 1413 is constructed, configured, and coupled to enable communication over a network 1403 with a plurality of computing devices 1407, 1409, 1411. The server 1413 includes a processing unit 1415 with an operating system 1417. The operating system 1417 enables the server 1413 to communicate through network 1403 with the remote, distributed user devices. Database 1429 houses an operating system 1431, memory 1433, and programs 1435.

In one embodiment of the invention, the system 1401 includes a cloud-based network 1403 for distributed communication via a wireless communication antenna 1405 and processing by at least one mobile communication computing device 1409. Alternatively, wireless and wired communication and connectivity between devices and components described herein include wireless network communication such as WI-FI, WORLDWIDE INTEROPERABILITY FOR MICROWAVE ACCESS (WIMAX), Radio Frequency (RF) communication including RF identification (RFID), NEAR FIELD COMMUNICATION (NFC), BLUETOOTH including BLUETOOTH LOW ENERGY (BLE), ZIGBEE, Infrared (IR) communication, cellular communication, satellite communication, Universal Serial Bus (USB), Ethernet communications, communication via fiber-optic cables, coaxial cables, twisted pair cables, and/or any other type of wireless or wired communication. In another embodiment of the invention, the system 1401 is a virtualized computing system capable of executing any or all aspects of software and/or application components presented herein on the computing devices 1407, 1409, 1411. In certain aspects, the computer system 1401 is implemented using hardware or a combination of software and hardware, either in a dedicated computing device, or integrated into another entity, or distributed across multiple entities or computing devices.

In another embodiment, the computer system 1401 is within an edge computing network. The server 1413 is an edge server, and the database 1429 is an edge database. The edge server 1413 and the edge database 1429 are part of an edge computing platform. In one embodiment, the edge server 1413 and the edge database 1429 are designated to distributed computing devices 1407, 1409, and 1411. In one embodiment, the edge server 1413 and the edge database 1429 are not designated for distributed computing devices 1407, 1409, and 1411. The distributed computing devices 1407, 1409, and 1411 connect to an edge server in the edge computing network based on proximity, availability, latency, bandwidth, and/or other factors.

By way of example, and not limitation, the computing devices 1407, 1409, 1411 are intended to represent various forms of digital computers 1407, 1411, 1413 and mobile devices 1409, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in this document In one embodiment, the computing device 1407 includes components such as a processor 1419, a system memory 1421 having a random access memory (RAM) 1423 and a read-only memory (ROM) 1425, and a system bus 1427 that couples the memory 1421 to the processor 1419. In another embodiment, the computing device 1409 additionally includes components such as a storage device 1437 for storing the operating system 1439 and one or more application programs 1441, a network interface unit 1443, and/or an input/output controller 1445. Each of the components is coupled to each other through at least one bus 1427. The input/output controller 1445 receives and process input from, or provide output to, a number of other devices 1447, including, but not limited to, alphanumeric input devices, mice, electronic styluses, display units, touch screens, signal generation devices (e.g., speakers), or printers.

By way of example, and not limitation, the processor 1419 is a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that perform calculations, process instructions for execution, and/or other manipulations of information.

In another implementation, shown as 1411 in FIG. 14, multiple processors 1419 and/or multiple buses 1427 are used, as appropriate, along with multiple memories 1421 of multiple types (e.g., a combination of a DSP and a microprocessor, a plurality of microprocessors, one or more microprocessors in conjunction with a DSP core).

Also, multiple computing devices are connected, with each device providing portions of the necessary operations (e.g., a server bank, a group of blade servers, or a multi-processor system). Alternatively, some steps or methods are performed by circuitry that is specific to a given function.

According to various embodiments, the computer system 1401 operates in a networked environment using logical connections to local and/or remote computing devices 1407, 1409, 1411, 1413 through a network 1403. A computing device 1409 connects to a network 1403 through a network interface unit 1443 connected to a bus 1427. Computing devices communicate communication media through wired networks, direct-wired connections or wirelessly, such as acoustic, RF, or infrared, through an antenna 1406 in communication with the network antenna 1405 and the network interface unit 1443, which includes digital signal processing circuitry when necessary. The network interface unit 1443 provides for communications under various modes or protocols.

In one or more exemplary aspects, the instructions are implemented in hardware, software, firmware, or any combinations thereof. A computer readable medium provides volatile or non-volatile storage for one or more sets of instructions, such as operating systems, data structures, program modules, applications, or other data embodying any one or more of the methodologies or functions described herein. The computer readable medium includes the memory 1421, the processor 1419, and/or the storage media 1437 and is a single medium or multiple media (e.g., a centralized or distributed computer system) that store the one or more sets of instructions 1449. Non-transitory computer readable media includes all computer readable media, with the sole exception being a transitory, propagating signal per se. The instructions 1449 are further transmitted or received over the network 1403 via the network interface unit 1443 as communication media, which includes a modulated data signal such as a carrier wave or other transport mechanism and includes any delivery media. The term "modulated data signal" means a signal that has one or more of its characteristics changed or set in a manner as to encode information in the signal.

Storage devices 1437 and memory 1421 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that is used to store the computer readable instructions and which is operable to be accessed by the computer system 1401.

It is also contemplated that the computer system 1401 may not include all of the components shown in FIG. 14, may include other components that are not explicitly shown in FIG. 14, or may utilize an architecture completely different than that shown in FIG. 14. The various illustrative logical blocks, modules, elements, circuits, and algorithms described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans are operable to implement the described functionality in varying ways for each particular application (e.g., arranged in a different order or partitioned in a different way), but such implementation decisions should not be interpreted as causing a departure from the scope of the present invention.

Figure 15A:
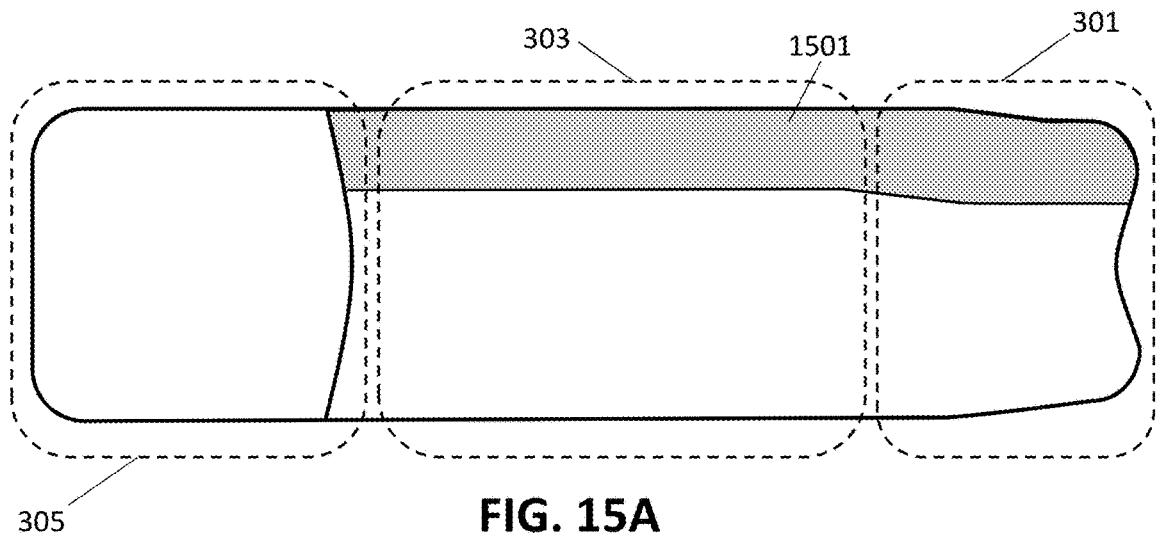
FIG. 15A illustrates a bottom view of a footwear object with a hallux valgus toe strap according to one embodiment of the present invention.
Figure 15B:
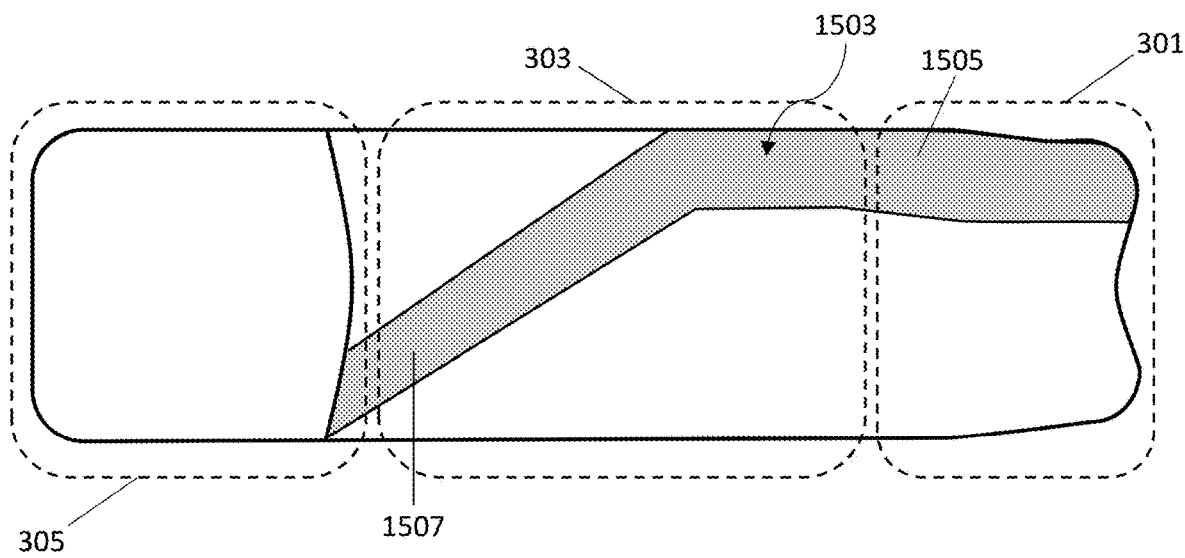
FIG. 15B illustrates a bottom view of a footwear object with an angled hallux valgus toe strap according to one embodiment of the present invention.
Figure 15C:
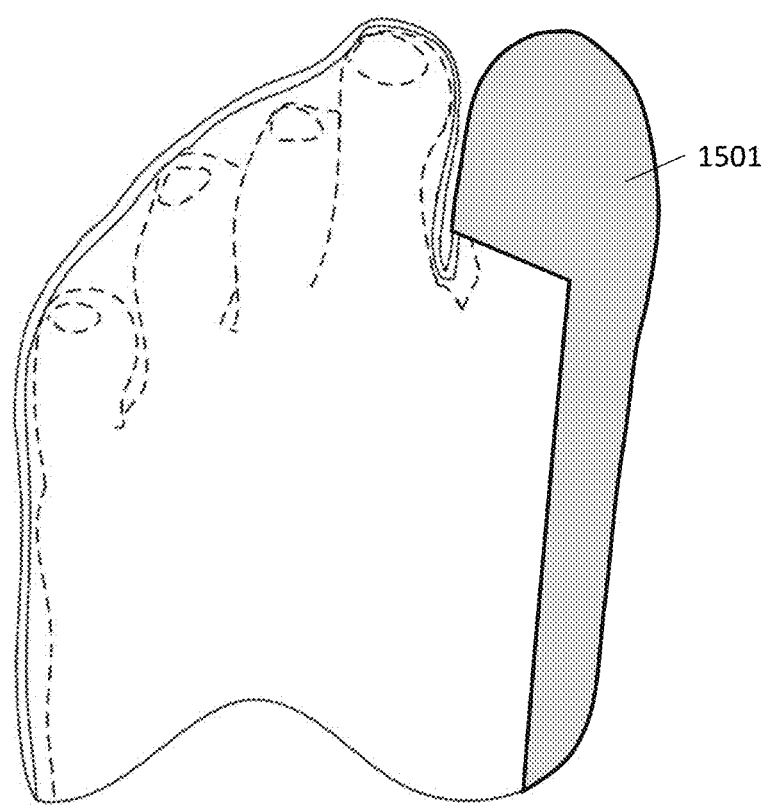
FIG. 15C illustrates a top view of a footwear object with a hallux valgus toe strap according to one embodiment of the present invention.
Figure 15D:
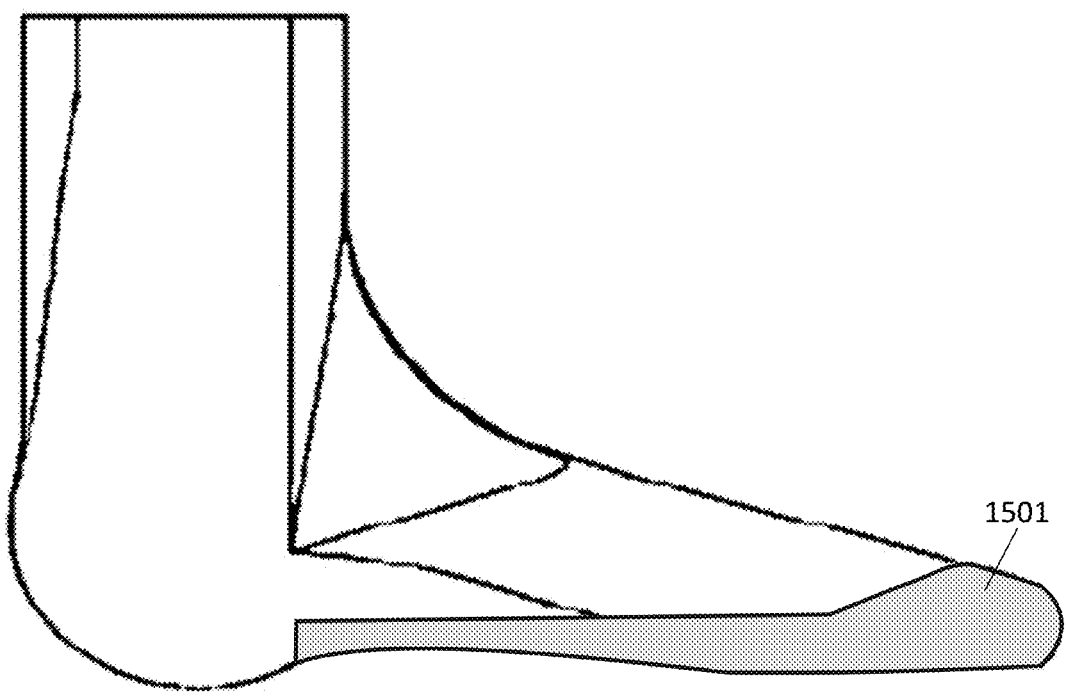
FIG. 15D illustrates a side view of a footwear object with a hallux valgus toe strap according to one embodiment of the present invention.

FIGS. 15A-15D illustrate alternative embodiments for a toe strap, wherein the toe straps are constructed to provide support for hallux valgus (bunion) injuries. FIG. 15A illustrates a first embodiment, wherein the toe strap 1501 is constructed to extend between a heel region 305, an arch region 303, or a point between the heel region 305 and an arch region 303, and wherein the toe strap 1501 applies a rearward force towards the heel region 305. FIG. 15B illustrates an alternative embodiment, wherein a toe strap 1503 includes a front section 1505 and a rear section 1507, wherein the front section 1505 extends along a side of the footwear object to the arch region 1503 and applies a rearward force toward a heel region 305. A rear section 1507 extends in a diagonal direction toward a heel region 305. In another embodiment, the rear section 1507 is located fully in a heel region 305 of the footwear object. FIG. 15C illustrates a top view of the toe strap for hallux valgus injuries, wherein the toe strap 1501 covers a hallux region and/or a hallux compartment and extends along a side of the footwear object. FIG. 15D illustrates a side view of the toe strap 1501 extending along a side of the footwear object.

Figure 16A:
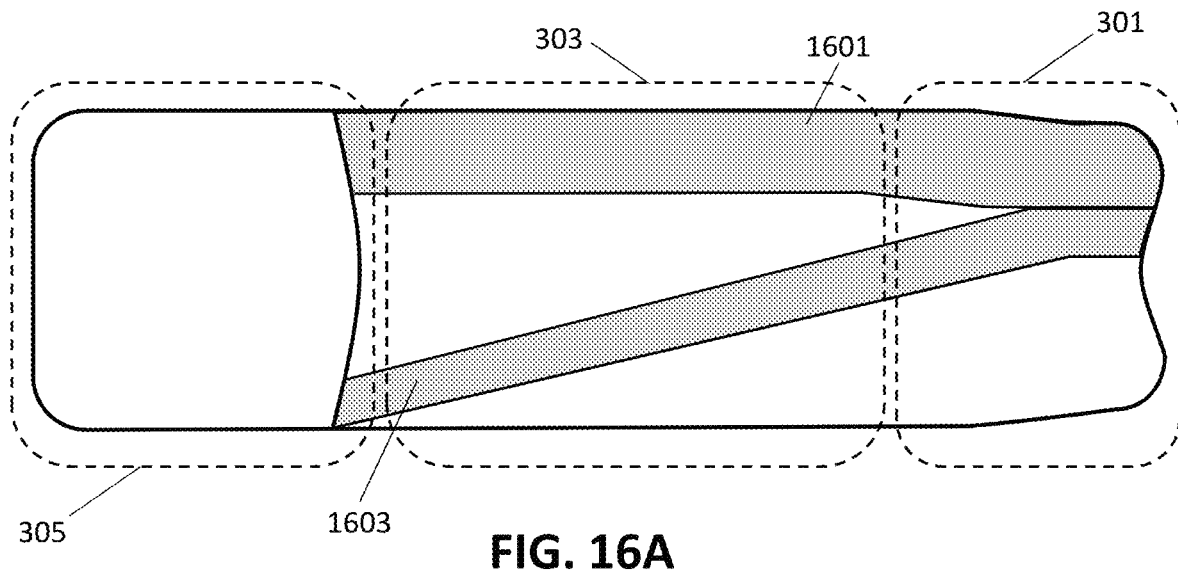
FIG. 16A illustrates a bottom view of a footwear object with a dual toe strap according to one embodiment of the present invention.
Figure 16B:
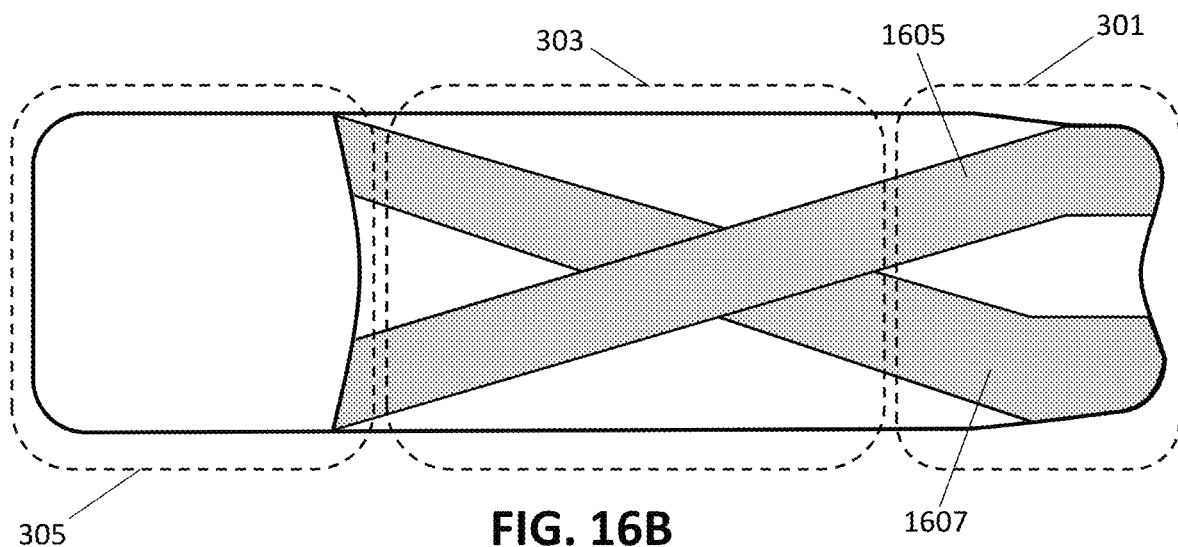
FIG. 16B illustrates a bottom view of a footwear object with crossing toe straps according to one embodiment of the present invention.

FIG. 16A illustrates one embodiment of a dual toe strap construction, wherein a first toe strap 1601 extends rearwardly along a side of the footwear object, and wherein a second toe strap extends diagonally from the toe region 301 to the heel region 305, the arch region 305, or a point between the heel region 305 and the arch region 305. FIG. 16B illustrates an alternative embodiment of a dual toe strap construction, wherein a first toe strap 1605 extends from the toe region 301, a first toe compartment, and/or a hallux region to the heel region 305, the arch region 305, or a point between the heel region 305 and the arch region 305; and wherein a second toe strap 1607 extends from the toe region 301, a second toe compartment, and/or a small toe region to the heel region 305, the arch region 305, or a point between the heel region 305 and the arch region 305.

Notably, while in one embodiment the footwear object illustrated and described is knitted or woven, the construction methods alternatively include any chemical, physical, or mechanical non-woven textile construction method and materials. For example, in one embodiment, toe straps, compression areas, grip elements, and/or other elements of the footwear object are integrated within a base layer the footwear object via thermal bonding methods.

While certain illustrative embodiments have been described, it is evident that many alternatives, modifications, permutations and variations will become apparent to those skilled in the art in light of the foregoing description.

The above-mentioned examples are provided to serve the purpose of clarifying the aspects of the invention, and it will be apparent to one skilled in the art that they do not serve to limit the scope of the invention. By nature, this invention is highly adjustable, customizable and adaptable. The above-mentioned examples are just some of the many configurations that the mentioned components can take on. All modifications and improvements have been deleted herein for the sake of conciseness and readability but are properly within the scope of the present invention.

The invention claimed is:

1. A footwear article, comprising:
   a textile structure including a toe region, an arch region, a heel region, and an ankle region;
   at least one toe strap, wherein the at least one toe strap is integrated within the textile structure, and wherein the at least one toe strap is constructed with a material that is more inelastic than the textile structure;
   a padded zone, wherein the padded zone covers a portion of a back of the ankle region above the heel region; and
   at least one external grip element including at least one external toe grip element, at least one external heel grip element, and at least one external arch grip element; and
   at least two compression areas;
   wherein the toe region includes two toe compartments;
   wherein the at least one toe strap extends from the heel region to the toe region, and wherein the at least one toe strap further extends from a bottom of one of the two toe compartments to a top of the one of the two toe compartments;
   wherein the at least one external grip element is integrated within a bottom of the textile structure;
   wherein the at least one external grip element includes a higher coefficient of friction than the padded zone and the at least two compression areas;
   wherein the at least one external grip element includes a patterned array of a plurality of shapes; and
   wherein the at least two compression areas are located on the arch region and on the ankle region.

2. The footwear article of claim 1, wherein the one of the two toe compartments includes a hallux compartment, wherein the at least one toe strap wraps over the front of the hallux compartment and terminates at a position on top of the hallux compartment.

3. The footwear article of claim 1, wherein the at least one toe strap includes a continuous band of material constructed to apply tension to the one of the two toe compartments toward a rear of the footwear article, wherein the at least one toe strap is woven into the footwear article, and wherein the at least one toe strap is adjustable.

4. The footwear article of claim 1, further comprising a plurality of internal gripping elements on an inside surface of the heel region, and wherein the plurality of internal gripping elements are made of silicone.

5. The footwear article of claim 1, further comprising one or more sensors, wherein the one or more sensors are adapted to collect usage metrics and communicate the collected usage metrics.

6. The footwear article of claim 5, wherein the collected usage metrics include information regarding at least two of pressure, impact, velocity, acceleration, temperature, humidity, location, sweat, stress, strain, or conductivity-resistance.

7. The footwear article of claim 1, wherein one of the at least two compression areas is located on the ankle region, and wherein the one of the at least two compression areas encircles the footwear article, and wherein the at least two compression areas include a thermal yarn.

8. The footwear article of claim 1, wherein the at least one external heel grip element wraps around the heel region and wherein the at least one external toe grip element is located on the bottom on the toe region and runs laterally to the at least one toe strap.

9. A footwear article, comprising:
   a textile structure including a toe region, an arch region, a heel region, and an ankle region;
   at least one toe strap integrated into the textile structure, wherein the at least one toe strap includes a first toe strap and a second toe strap, and wherein the first toe strap is constructed with a material that is more inelastic than the textile structure;
   a padded zone, wherein the padded zone covers a portion of a back of the ankle region above the heel region;
   at least one external grip element including at least one external toe grip element, at least one external heel grip element, and at least one external arch grip element and at least two compression areas;

wherein the toe region includes at least two toe compartments;

wherein the first toe strap includes a continuous band of material which extends from the heel region to the toe region, and wherein the first toe strap further extends from a bottom of one of the at least two toe compartments to a top of the one of the at least two toe compartments;

wherein the first toe strap applies tension in a direction toward a bottom of the footwear article and a rear of the footwear article;

wherein the at least one external grip element includes a patterned array of a plurality of shapes; and wherein the at least two compression areas are located on the arch region and on the ankle region.

10. The footwear article of claim 9, wherein the textile structure is constructed from a non-woven material.

11. The footwear article of claim 9, wherein the textile structure is knitted or woven, and wherein the at least one toe strap is knitted or woven into the textile structure.

12. The footwear article of claim 9, wherein the second toe strap is configured to extend diagonally from in front of the heel region on the bottom of the footwear article, cross over the bottom of the footwear article, and terminate at the toe region on top of the hallux.

13. The footwear article of claim 9, wherein the second toe strap applies tension in a second direction toward the bottom of the footwear article and the rear of the footwear article.

14. The footwear article of claim 9, further comprising internal grip elements on an inside surface of the footwear article within the heel region.

15. The footwear article of claim 9, wherein the at least one toe strap elongates to between about 0.3 centimeters and about 0.6 centimeters (about 0.118 inches and about 0.236 inches) when bent approximately 90 degrees during use.

16. A footwear article, comprising:
a textile structure including a toe region, an arch region, a heel region, and an ankle region, wherein the toe region includes at least two toe compartments;
a padded zone, wherein the padded zone covers a portion of a back of the ankle region above the heel region;
at least two compression areas;
at least one toe strap; and
at least one integrated external grip element;
wherein the at least one integrated external grip element includes at least one integrated external toe grip element, at least one integrated external heel grip element, and/or at least one integrated external arch grip element;
wherein the at least one integrated external grip element includes a patterned array of a plurality of shapes;
wherein the at least one toe strap is constructed with a material that is more inelastic than the textile structure;
wherein a first compression area of the at least two compression areas is located on the arch region and a second compression area of the at least two compression areas is located on the ankle region;
wherein the textile structure, the at least one toe strap, and the at least two compression areas are knitted or woven; and
wherein the at least two compression areas encircle the footwear article.

17. The footwear article of claim 16, wherein the at least two compression areas are made of yarns comprising nylon, polyester, and/or spandex.

18. The footwear article of claim 16, wherein the second compression area of the at least two compression areas extends from a bottom of the ankle region to a top of the footwear article.

19. The footwear article of claim 16, wherein the first compression area of the at least two compression areas overlaps with the at least one integrated external grip element.

20. The footwear article of claim 16, wherein the at least one integrated external grip element includes a higher coefficient of friction than the padded zone and the at least two compression areas.

* * * * *